(12) United States Patent
Hull et al.

(10) Patent No.: US 12,147,927 B1
(45) Date of Patent: Nov. 19, 2024

(54) MACHINE LEARNING SYSTEM AND METHOD FOR PREDICTING CAREGIVER ATTRITION

(71) Applicant: ClearCare, Inc., San Francisco, CA (US)

(72) Inventors: Jonathan J. Hull, San Carlos, CA (US); Geoffrey Nudd, San Francisco, CA (US)

(73) Assignee: CLEARCARE, INC., San Francisco, CA (US)

( * ) Notice: Subject to any disclaimer, the term of this patent is extended or adjusted under 35 U.S.C. 154(b) by 0 days.

(21) Appl. No.: 17/877,834

(22) Filed: Jul. 29, 2022

Related U.S. Application Data

(63) Continuation of application No. 16/102,559, filed on Aug. 13, 2018, now Pat. No. 11,436,549.

(60) Provisional application No. 62/558,342, filed on Sep. 13, 2017, provisional application No. 62/545,350, filed on Aug. 14, 2017.

(51) Int. Cl.

| | |
|---|---|
| *G06Q 30/00* | (2023.01) |
| *G06F 16/9535* | (2019.01) |
| *G06N 20/00* | (2019.01) |
| *G06Q 10/0635* | (2023.01) |
| *G06Q 10/0639* | (2023.01) |
| *H04W 4/38* | (2018.01) |

(52) U.S. Cl.
CPC ... *G06Q 10/06398* (2013.01); *G06F 16/9535* (2019.01); *G06N 20/00* (2019.01); *G06Q 10/0635* (2013.01); *H04W 4/38* (2018.02)

(58) Field of Classification Search
CPC ........ G06Q 10/06398; G06Q 10/0635; H04W 4/38; G06N 20/00; G06F 16/9535
See application file for complete search history.

(56) References Cited

U.S. PATENT DOCUMENTS

| | | |
|---|---|---|
| 6,598,020 B1 | 7/2003 | Kleindienst et al. |
| 8,374,865 B1 | 2/2013 | Biadsy et al. |
| 9,723,149 B2 | 8/2017 | Meng et al. |

(Continued)

FOREIGN PATENT DOCUMENTS

| | | | | |
|---|---|---|---|---|
| AU | 2009202262 A1 | * | 12/2009 | ............. G06Q 10/06 |
| WO | 2005059681 A2 | | 6/2005 | |

(Continued)

OTHER PUBLICATIONS

Glascock et al., The Impact of Behavioral Monitoring Technology on the Provision of Health Care in the Home. 2006, Journal of Universal Computer Science, vol. 12, No. 1 (2006), 59-79, (Year: 2006).*

(Continued)

*Primary Examiner* — Crystol Stewart
*Assistant Examiner* — Uche Byrd
(74) *Attorney, Agent, or Firm* — PATENT LAW WORKS LLP

(57) ABSTRACT

A system collects information associated with the work performance and work satisfaction of caregiver's who provide in-home care services to seniors. A machine learning system is trained to predict caregiver attrition and generate a user interface display indicative of a risk an individual caregiver will attrit. The system may also be used to determine action steps to reduce the risk of attrition of a caregiver.

19 Claims, 23 Drawing Sheets

(56) References Cited

U.S. PATENT DOCUMENTS

| | | | |
|---|---|---|---|
| 9,798,343 B2 | 10/2017 | Kaufman | |
| 9,934,780 B2 | 4/2018 | Tzirkel-Hancock | |
| 10,235,990 B2 | 3/2019 | Corelli et al. | |
| 10,311,869 B2 | 6/2019 | Weng et al. | |
| 10,311,980 B2 | 6/2019 | Kim et al. | |
| 10,319,477 B1 | 6/2019 | Bill | |
| 10,329,784 B1 | 6/2019 | Corwin | |
| 10,543,137 B2 | 1/2020 | Hayes | |
| 11,120,226 B1 | 9/2021 | Nudd | |
| 2003/0114736 A1* | 6/2003 | Reed | G16H 10/60 600/300 |
| 2003/0200142 A1* | 10/2003 | Hicks | G06Q 30/0226 705/14.27 |
| 2008/0235018 A1 | 9/2008 | Eggen et al. | |
| 2009/0256710 A1* | 10/2009 | Duckert | G08B 21/0484 340/573.1 |
| 2009/0307025 A1* | 12/2009 | Menon | G06Q 10/06 705/7.28 |
| 2011/0125844 A1* | 5/2011 | Collier | H04W 4/38 709/204 |
| 2011/0151418 A1 | 6/2011 | Delespaul | |
| 2014/0067730 A1 | 3/2014 | Kozloski | |
| 2014/0163337 A1* | 6/2014 | Horseman | A61B 5/6887 600/301 |
| 2014/0377727 A1* | 12/2014 | Yom-Tov | G16H 50/20 434/236 |
| 2016/0198047 A1 | 7/2016 | McCormack | |
| 2016/0287166 A1* | 10/2016 | Tran | A61B 5/74 |
| 2018/0075763 A1 | 3/2018 | Wainfan | |
| 2018/0226076 A1 | 8/2018 | Kotti et al. | |
| 2018/0294059 A1 | 10/2018 | Savant et al. | |
| 2018/0308487 A1 | 10/2018 | Goel et al. | |
| 2018/0357286 A1 | 12/2018 | Wang et al. | |
| 2019/0008583 A1 | 1/2019 | Gallagher et al. | |
| 2019/0130243 A1 | 5/2019 | Penubothula et al. | |
| 2019/0189253 A1 | 6/2019 | Kartoun | |

FOREIGN PATENT DOCUMENTS

| | | | |
|---|---|---|---|
| WO | 2005059681 A3 | 6/2006 | |
| WO | WO-2013033655 A1 * | 3/2013 | A61B 5/0002 |

OTHER PUBLICATIONS

Asatryan, "4 Disorders That May Thrive on Loneliness", https://www.psychology1oday.com/us/blog/the-art-closeness/201507/4-disorders-may-thrive-loneliness, Jul. 23, 2015, 5 pgs.

Baez et al., "Personalized Persuasion for Social Interactions in Nursing Homes", Proceedings of the Personalization ir Persuasive Technology Workshop, Persuasive Technology 2016, Salzburg, Austria, http://ceur-ws.org/Vol-1582/11Baez.pdf, May 4, 2016, 6 pgs.

Bansal, "Beginners Guide to Topic Modeling in Python", Analytics Vidhya, hllps://www.analyticsvidhya.com/blog/2016/08/beginners-guide-to-topic-modeling-in-py1hon/, Aug. 24, 2016, 8 pgs.

Chen et al., "Gunrock: Building a Human-Like Social Bot by Leveraging", 2nd Proceedings of Alexa Prize {Alexa Prize 2018), Department of Computer Science, University of California, Davis, https://s3.amazonaws.com/dex-microsites-brod/alexaprize/2018/papers/Gunrock.pdf, 2018, 19 pgs.

Hawkley et al., "Loneliness Predicts Reduced Physical Activity: Cross-Sectional & Longitudinal Analyses," Health Dsychol., May 2009, vol. 28, No. 3, pp. 354-363.

Lardieri, "Study: Many Americans Report Feeling Lonely, Younger Generations More So", US News & World Report, hllps://www.usnews.com/news/health-care-news/articles/2018-05-01/study-many-americans-report-feeling-lonely-younger-generations-more-so, May 1, 2018, 6 pgs.

Lowe et al., "The Ubuntu Dialogue Corpus: A Large Dataset for Research in Unstructured Multi-Turn Dialogue Systems", School of Computer Science, McGill University, Montreal, Canada, hllps://arxiv.org/abs/1506.08909, Feb. 4, 2016, 10 pgs.

Manning et al., "The Stanford CoreNLP Natural Language Processing Toolkit", Proceedings of 52nd Annual Meeting of the Association for Computational Linguistics: System Demonstrations, hllps://www.ncbi.nlm.nih.gov/pmc/articles/DMC4159765/, Jun. 23-24, 2014, pp. 55-60.

Petersen et al., "SVM to Detect the Presence of Visitors in a Smart Home Environment," Cont. Proc. IEEE Eng. Med. Biol. Soc., 2012, 9 pgs.

Reddit "I Have Every Publicly Available Reddit Comment", https://www.reddit.com/r/datasels/comments/3bxlg7/_have_every_publicly_available_reddit_comment/, ca. 2015, 5 pgs.

Ring et al., "Addressing Loneliness and Isolation in Older Adults: Proactive Affective Agents Provide Better Support," 2013 Humaine Association Conference on Affective Computing and Intelligent Interaction, Geneva, https://ieeexplore.eee.org/document/6681408/citations?labFilter=papers#citations, 2013, 6 pgs.

Russell, "UCLA Loneliness Scale {Version 3): Reliability, Validity, and Factor Structure," Journal of Personality Assessmenl, 1996, vol. 66, No. 1, pp. 20-40.

Vargheese et al., "Persuasive Strategies for Encouraging Social Interaction for Older Adults", International Journal of Human-Computer Interaction, vol. 32, 2016—Issue 3, https://www.landfonline.com/doi/ull/10.1080/10447318.2016.1136176, Jan. 4, 2016, 6 pgs.

An Always On Relational Agent for Social Support, Relational Agents Group, Jan. 9, 2019, 1 pg.

Asatryan, "4 Disorders That May Thrive on Loneliness", https://www.psychologytoday.com/us/blog/the-art-closeness/201507/4-disorders-may-thrive-loneliness, Jul. 23, 2015, 5 pgs.

Austin et al., "A Smart-Home System to Unobtrusively and Continuously Assess Loneliness in Older Adults," IEEE Journal of Translational Engineering in Health and Medicine, Jun. 10, 2016, vol. 4, 11 pgs.

Aylaz et al., "Relationship Between Depression and Loneliness in Elderly and Examination of Influential Factors", US National Library of Medicine National Institutes of Health, https://www.ncbi.nlm.nih.gov/pubmed/22487148, Apr. 8, 2012, 2 pgs.

Baez et al., "Personalized Persuasion for Social Interactions in Nursing Homes", Proceedings of the Personalization in Persuasive Technology Workshop, Persuasive Technology 2016, Salzburg, Austria, http://ceur-ws.org/Vol-1582/11Baez.pdf, May 4, 2016, 6 pgs.

Bansal, "Beginners Guide to Topic Modeling in Python", Analytics Vidhya, hllps://www.analyticsvidhya.com/blog/2016/08/beginners-guide-to-topic-modeling-in-python/, Aug. 24, 2016, 8 pgs.

Bird et al., "Natural Language Processing with Python: Chapter 5 Categorizing and Tagging Words", https://www.nltk.org/book/ch05.html, Apr. 1, 2019, 29 pgs.

Buchman et al., "Loneliness and the rate of motor decline in old age: the rush memory and aging project, a communily-based cohort study," BMC Geriatrics, 2010, vol. 10, No. 77, 8 pgs.

Chen et al., "Gunrock: Building a Human-Like Social Bot by Leveraging", 2nd Proceedings of Alexa Prize {Alexa Prize 2018), Department of Computer Science, University of California, Davis, https://s3.amazonaws.com/dex-microsites-prod/alexaprize/2018/papers/Gunrock.pdf, 2018, 19 pgs.

Chiu et al., "Named Entity Recognition with Bidirectional LSTM-CNNs", Transactions of the Association for computational Linguistics, vol. 4, Jul. 2016, pp. 357-370.

Fetzer Institute, "UCLA Loneliness Scale," Self Report Measures for Love and Compassion Research: Loneliness and Interpersonal Problems, at least as early as Feb. 16, 2019, 2 pgs.

Hawkley et al., "Loneliness Predicts Reduced Physical Activity: Cross-Sectional & Longitudinal Analyses," Health Psychol., May 2009, vol. 28, No. 3, pp. 354-363.

Hayes et al., "Unobtrusive assessment of activity patterns associated with mild cognitive impairment," Alzheimers Dement., Nov. 2008, vol. 4, No. 6, pp. 395-405.

Hughes et al., "A Short Scale for Measuring Loneliness in Large Surveys: Results From Two Population-Based Studies," Res. Aging, 2004, vol. 26, No. 6, pp. 655, 672.

(56) References Cited

OTHER PUBLICATIONS

Kaye et al., "Unobtrusive measurement of daily computer use to detect mild cognitive impairment," Alzheimers Dement., Jan. 2014, vol. 10, No. 1, 15 pgs.

Language-Independent Named Entity Recognition (II), https://www.clips.uantwerpen.be/conll2003/ner/, 2003, 7 pgs.

Lardieri, "Study: Many Americans Report Feeling Lonely, Younger Generations More So", US News & World Report, https://www.usnews.com/news/health-care-news/articles/2018-05-01/study-many-americans-report-feeling-lonely-younger-generations-more-so, May 1, 2018, 6 pgs.

Lowe et al., "The Ubuntu Dialogue Corpus: A Large Dataset for Research in Unstructured Multi-Turn Dialogue Systems", School of Computer Science, McGill University, Montreal, Canada, https://arxiv.org/abs/1506.08909, Feb. 4, 2016, 10 pgs.

Manning et al., "The Stanford CoreNLP Natural Language Processing Toolkit", Proceedings of 52nd Annual Meeting of the Association for Computational Linguistics: System Demonstrations, https://www.ncbi.nlm.nih.gov/pmc/articles/PMC4159765/, Jun. 23-24, 2014, pp. 55-60.

Nemecek, "Cigna's U.S. Loneliness Index", https://www.multivu.com/players/English/8294451-cigna-us-loneliness-survey/, May 2018, 61 pgs.

Petersen et al., "Phone behaviour and its relationship to loneliness in older adults," Aging Ment. Health, Oct. 2016, vol. 20, No. 10, pp. 1084-1091.

Petersen et al., "SVM to Detect the Presence of Visitors in a Smart Home Environment," Conf. Proc. IEEE Eng. Med. Biol. Soc., 2012, 9 pgs.

Petersen et al., "Unobtrusive in-home detection of time spent out-of-home with applications to loneliness and physical activity", IEEE J Biomed Health Inform, Sep. 2014, 17 pgs.

Reddit "I Have Every Publicly Available Reddit Comment", https://www.reddit.com/r/datasets/comments/3bxlg7/_have_every_publicly_available_reddit_comment/, ca. 2015, 5 pgs.

Ring et al., "Addressing Loneliness and Isolation in Older Adults: Proactive Affective Agents Provide Better Support," 2013 Humaine Association Conference on Affective Computing and Intelligent Interaction, Geneva, https://ieeexplore.ieee.org/document/6681408/citations?tabFilter=papers#citations, 2013, 6 pgs.

Russell, "UCLA Loneliness Scale (Version 3): Reliability, Validity, and Factor Structure," Journal of Personality Assessment, 1996, vol. 66, No. 1, pp. 20-40.

Shao et al., "Generating High-Quality and Informative Conversation Responses", Jul. 31, 2017, 11 pgs.

Topic Modeling with Gensim (Python), https://www.machinelearningplus.com/nlp/topic-modeling-gensim-python/, 2018, 43 pgs.

Vargheese et al., "Persuasive Dialogue for Older Adults", CHI 2013 Changing Perspectives, Paris, France, Apr. 27-May 2, 2013, 6 pgs.

Vargheese et al., "Persuasive Strategies for Encouraging Social Interaction for Older Adults", International Journal of Human-Computer Interaction, vol. 32, 2016—Issue 3, https://www.tandfonline.com/doi/full/10.1080/10447318.2016.1136176, Jan. 4, 2016, 6 pgs.

\* cited by examiner job feedback

Martha, was your last client happy with your service? [N]  Y, N, U

If no, what happened?

| Angry client yelled at me again even though I did nothing wrong |

How many hours would you like to work next week? [40] ↔

What is the maximum distance from your home? [5 miles] ↔

Do you feel appreciated? [N]  Y, N, U

[Enter]

Fig. 6A

In scheduling Martha have you noticed changes to her mood or Behavior? [Y] Y, N, U If yes, please explain below Martha told me she was frustrated the client yells at her when she makes the client do her exercises

[Enter]

Fig. 6B job feedback

Are you happy with the performance of the caregiver Martha you are managing?

[U]  Y, N, U

Caregiver Martha spoke to me in an frustrated tone when I asked why she was late for her last assigned shift. She said she is starting to hate her work because of one senior that is always yelling at her

[Enter]

Fig. 6D

Job feedback

Are you happy with the service your mother receives from Martha? If so, why?

[Y]  Y, N, U

Martha makes Mom do her exercises and eat her vegetables, even though this makes Mom very angry. Mom also yells at Martha when Martha turns on educational television shows which are good to stimulate Mom's brain. I wish you had more people like Martha. She is a saint!

Do you appreciate the work of the Caregiver for your Mom?

[Y]  Y, N, U

[Enter]

Fig. 6E

Caregiver Attrition Risk Groups

*Agency: World's Best Caregivers: 80 Active caregivers as of Aug. 3, 2018*

Risk indicator (G, Y, R) [R]

| Sept. 3 | Oct. 3 | Nov. 3 |
|---|---|---|
| Jane Doe | Bob Doe | Desiree Doe | Sophia Doe |
| Mary Doe | Erin Doe | Sharon Doe | Mia Doe |
| | Olivia Doe | Apple Doe | Charlotte Doe |
| | | Stella Doe | Amelia Doe |
| | | Emma Doe | Evelyn Doe |
| | | Ava Doe | Abigail Doe |
| | | Arya Doe | Harper Doe |
| | | Isabella Doe | Emily Doe |

Fig. 17

MACHINE LEARNING SYSTEM AND METHOD FOR PREDICTING CAREGIVER ATTRITION

CROSS REFERENCE TO RELATED APPLICATIONS

The present application is a continuation of U.S. patent application Ser. No. 16/102,559, entitled "Machine Learning system and Method for Predicting Caregiver Attrition," filed Aug. 13, 2018, which claims the benefit of U.S. Provisional Application No. 62/545,350 entitled, "Data Analysis System to Predict Caregiver Attrition," filed Aug. 14, 2017; U.S. Provisional Application No. 62/558,342 entitled, "Machine Learning System for Predicting and Signaling the Potential for Caregiver Attrition," filed Sep. 13, 2017. The contents of each of which are hereby incorporated by reference.

TECHNICAL FIELD

Embodiments of the disclosure are generally related to providing business intelligence and analytics related to managing caregivers who provide at-home assistance to seniors or other people who require in-home care.

BACKGROUND

Many people with health challenges rely on in-home care for part of their health care needs. As one example, many senior citizens benefit from having in-home care a few days a week. For example, a physician may create a health care plan for a senior that includes scheduled visits by an in-home caregiver. The caregiver may do a variety of tasks related to taking care of the senior at home. This may include making sure the senior takes prescribed medications, helping the senior to the bathroom, helping the senior perform physical or mental exercises assigned by the physician in the care plan, etc.

One problem in providing in-home care is managing caregivers. In the United States the average age of the population is rising and the percentage of senior citizens is increasing. There is thus an increasingly larger percentage of the population that might benefit from receiving in-home care. However, it is difficult for agencies to find and retain enough qualified caregivers. Caregivers can quit for a wide variety of reasons such that there is a high rate of caregiver attrition in the industry.

Embodiments of this disclosure were developed in view of the above-described problems.

SUMMARY

Embodiments of the disclosure generally are related to a predictive analytics system architecture, components, and methods to collect and analyze stored data and recently captured data about caregiver work performance and satisfaction. In one embodiment, based on trends in features from recently captured data, as compared to stored data, a machine learning system predicts the likelihood (e.g., a real number between 0 and 1) that individual caregivers or groups of caregivers (CGs) will attrit in the near future. In one embodiment, a rich variety of data sources are utilized, including feedback from participants acting in the different roles in providing in-home care services, in-home sensor data, mobile device data, or other sources of data.

In one embodiment, the machine learning system utilizes an ensemble of classifiers each trained for a different length of employment as a caregiver. In making predictions for an individual caregiver, a classifier is selected for the caregiver based on the current length of employment of the caregiver.

In one embodiment, the likelihood that an individual caregiver will attrit is converted to a graphical signal that is displayed on a user interface together. In one embodiment, a ranked list of features that contributed to computing that likelihood is also generated. In one embodiment, a risk of caregiver attrition is classified into at least two different categories and each category has a different graphical element representation such as a different color, shape, size, texture, shading, or alpha-numeric representation. In some embodiments, a user selects an individual graphical element and in response a list of features that contributed to the category associated with the graphical element is displayed.

In one embodiment, the graphical signal is a fixed set of colored graphical elements with a corresponding different level of risk, such as a red circle (there is an imminent hazard of attrition), a yellow circle (caution zone) indicating an increased risk (greater than 70%) of caregiver attrition in the next four weeks, and a green circle indicates there is no elevated risk of caregiver attrition.

In one embodiment, a display is generated that displays lists of caregivers falling into a particular risk category. This permits a manager or agency owner to obtain a comprehensive view of all caregivers having a high risk of attrition in a given time window. Conversely, a manager or agency owner can obtain a comprehensive view of caregivers at a low or moderate risk of attrition.

In some embodiment, a display is also generated of suggested action items for a manager or agency owner to respond to attrition risk prediction of individual caregivers and groups of caregivers.

BRIEF DESCRIPTION OF THE DRAWINGS

FIG. 6A illustrates an example of a caregiver job feedback app in accordance with an embodiment.

FIG. 6B illustrates an example of a scheduler job feedback app in accordance with an embodiment.

FIG. 6D illustrates an example of a manager job feedback app in accordance with an embodiment.

FIG. 6E illustrates an example of a family member job feedback app in accordance with an embodiment.

FIG. 17 illustrates an example of an agency/manager user interface in accordance with an embodiment.

DETAILED DESCRIPTION

Figure 1:
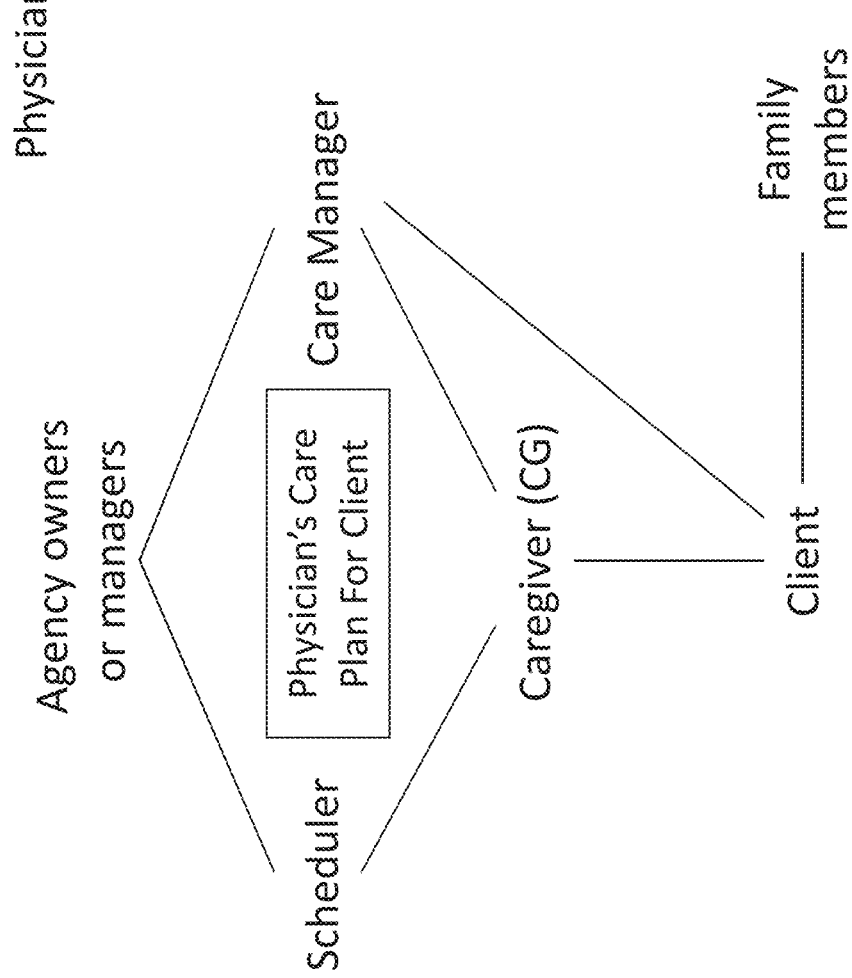
FIG. 1 illustrates an example of participants related to providing in-home care services in accordance with a physician's care plan.

FIG. 1 illustrates some of the potential participants related to providing in-home care services. There is a client who requires in-home care. The client may be a senior citizen but more generally it could also be anyone requiring in-home care, such as someone with a disability, chronic illness, or injury requiring long-term care. The client may also be described as a patient in the sense that receive assistance related to their health care needs.

In-home care may be specified by a physician who creates a care plan for a patient. For example, a medical doctor may create a care plan in which a caregiver visits a senior citizen twice a week and cares for the senior according to tasks outlined in the care plan.

An in-home care agency (with an agency owner or manager) is typically responsible for managing caregivers. This may include using a scheduler to schedule a caregiver to visit a client. A care manager (or care coordinator) manages caregivers.

Family members of the client are also potential participants in providing in-home assistance. Family members may, for example, provide feedback about the quality of the senior's care.

Figure 2:
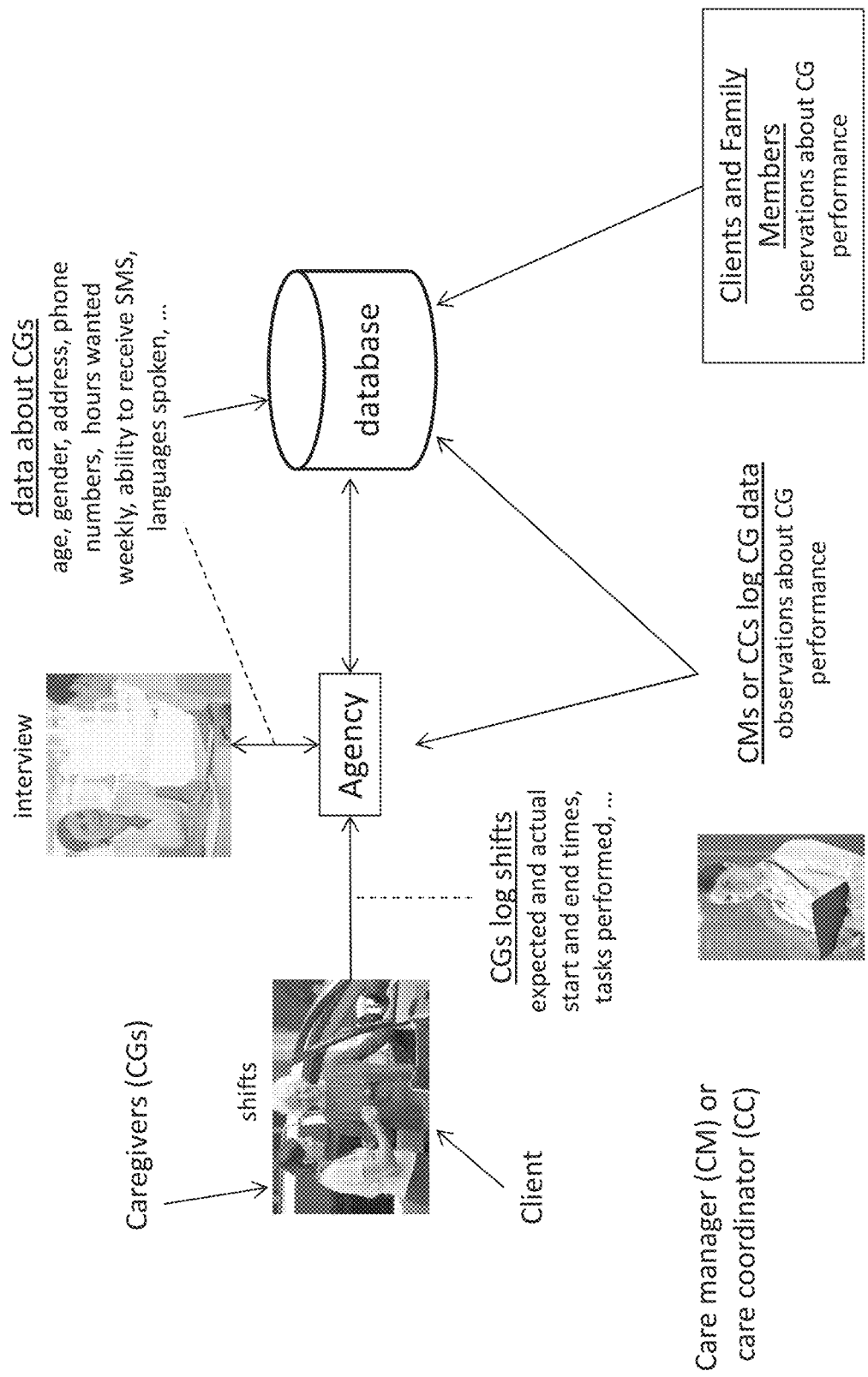
FIG. 2 illustrates caregiver and agency system interactions in accordance with an embodiment.

FIG. 2 is a diagram of an embodiment of caregiver and agency interactions in a system in which data is collected about the interactions. Agencies capture data about caregivers (CGs) when they are interviewed such as their age, gender, address, etc. That information is stored by an Applicant Tracking System (not shown in FIG. 2) in an online database. This Applicant data may, in some cases, be shared among many different agencies. After the caregiver is hired, the expected and actual start and end times for their shifts as well as the tasks that were performed on those shifts are stored in the database as they are performed. This provides a dynamic, constantly updated source of information of the performance of caregivers. A shift is a basic unit of work for a caregiver and might for example be a two-hour slot of time when the caregiver accompanies a patient to shopping.

Care managers (CMs) and care coordinators (CCs) oversee the performance of the caregivers and they enter observations about the performance of the caregiver in the database, such as a recent change in attitude or comments made by the CG or colleagues of the CG that reflect on their potential for attrition. For example, the CM might enter a comment about caregiver Mary that says "Mary said the commute to patient X is getting tougher every day."

Clients and family members enter observations about the performance of the CG that are directly and indirectly related to the CG's performance on specific shifts. For example, the client might say that the CG did a great job or the client might say the CG is talking more about her family in Georgia than she formerly did. Family members may provide positive or negative feedback above the personality, behavior, or work habits of the CG. ("I stopped by Mom's home the other day when the Caregiver was there. The caregiver didn't care at all that Mom was eating a sugary donut in violation of her care plan! Doesn't the caregiver know that Mom is diabetic?").

The collected interaction data may be used for various purposes, including collecting data for the purposes of using machine learning or artificial intelligence techniques to make predictions on CG attrition. An attrition risk for an individual CG may be expressed as a likelihood a CG will attrit in a particular time period (where the term "attrit" is the verb form of attrition in the sense the CG may cease working for the agency).

Figure 3:
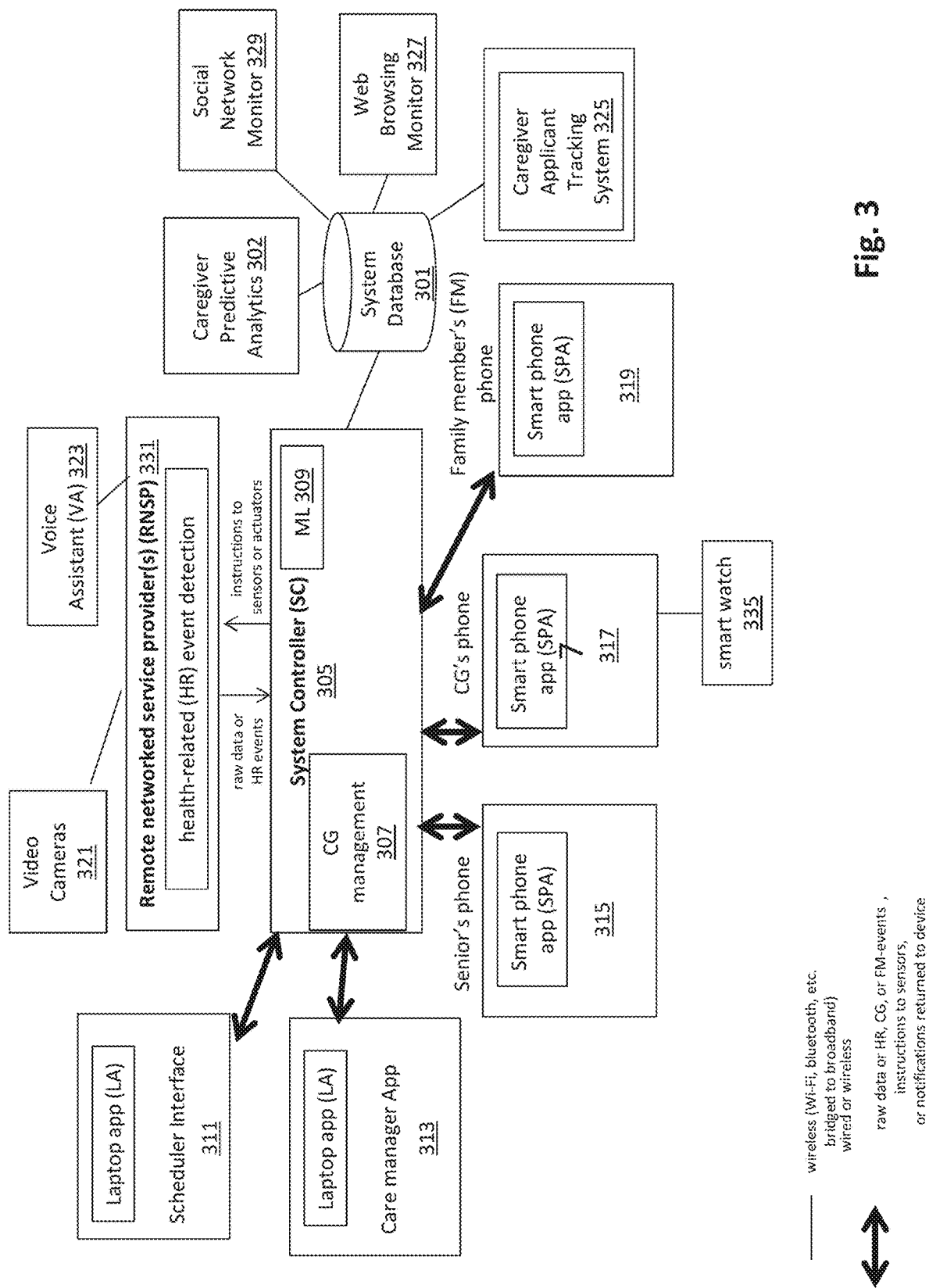
FIG. 3 illustrates an example of a system for managing and monitoring caregivers in accordance with an embodiment.

FIG. 3 illustrates an example of a system in accordance with an embodiment. In one embodiment, the system collects data in a database 301 about caregivers who provide in-home care services. A caregiver predictive analytics unit 302 analyzes the data and generates predictions of a risk caregivers will attrit within pre-selected or configurable time periods. As a non-limiting example, a manager with 100 caregivers may wish to receive a weekly or monthly report of individual caregivers or groups of caregivers having a high risk of attrition in the future (e.g. within one month, two months, etc.). This, in turn, permits a manager or agency owner to be proactive in taking steps to retain caregivers and/or make recruiting decisions.

In one embodiment, the caregiver predictive analytics unit 302 performs feature extraction of the data. Statistical and machine learning techniques are performed on the extracted data features to predict caregiver attrition in a time window (e.g., a configurable number of weeks or months). The features may, for example, include time-based features (e.g., clock-in/clock-out data, current utilization, etc.), static data (e.g., demographic data about the caregiver). The features may include the total number of hours worked per week, number of different clients, or details about the types of clients served that may be related to a level of difficulty of the caregiver's job. Other example of features includes feedback data (e.g., job feedback data from the CG, the client, family members of the client, etc.); and data features derived from any sensors in the home of the person being cared for (e.g., microphones, cameras, or other sensors) or sensors in a smart watch or mobile device of the CG; and data derived from social media and web browsing behavior of the caregiver. In one embodiment, a graphical user interface is generated, based on an output of a machine learning system of the caregiver predictive analytics unit 302. In one embodiment, the graphical user interface includes graphical elements indicating a level of risk that a caregiver will attrit in a selected time window, such as for a high, medium, or low risk of caregiver attrition. The graphical elements, may for example, include colors, icons, shapes, sizes, textures, shading, alpha-numeric symbols, or other graphical signals. In some embodiments, the machine learning system also generates a list of major features that led to a particular attrition risk determination. Additionally, in one embodiment the system may recommend actions based on attrition risks.

In one embodiment, a system controller (SC) 305 is used to coordinate at least some aspects of caregiver management. Additionally, the SC 305 may also coordinate interactions with computing devices of a scheduler, via a scheduler interface 311, a computing device of a care manager 313, a senior's computing device, such as a senior's phone 315, a caregiver's phone 317, or a family member's computing device or phone 319. In one embodiment, in-home care is augmented with in-home smart devices based on Internet of Things (IoT) technology. As a partial list of examples, this may include a video camera 321 and voice assistant 323 in the home of the senior.

In one embodiment, the architecture utilizes at least one remote networked service provider (RNSP) 331 to access IoT devices such as video cameras 321 and a voice assistant 323. Examples of RNSPs include Amazon, Alexa, and G-Co.

The RNSP 331 optionally is modified to include methods for detection of health-related (HR) events. The detection of HR events converts raw sensor data to events that are relevant to the health and care of the senior. As examples, this may be in the context of the senior being cared for by a caregiver, when the senior is alone, or when the senior is being attended to by a family member. The HR events may be directly related to a short-term danger to senior's health. For example, an event would be the senior depicted in the video captured on the cameras falling down on the floor. HR events may also be related to a care plan for the senior (e.g., medications, diet plan, exercise plan), general health information (e.g., sleep patterns, toilet behavior etc.) HR events may also include detecting risk factors (e.g., poor quality air in the senior's home, low lighting or other factors increasing the risk of a potential fall, etc.). However, more generally, the HR events may encompass social, behavioral, or other aspects.

In one embodiment, the SC 305 contains a Care Giver (CG) management module 307 that recommends CGs for particular seniors, allows CGs to sign up for shifts, tracks the times when CGs arrive and depart, suggests and tracks the task and care protocols to be performed, provides medication reminders and/or verifies medication adherence in conjunction with other devices or sensors, etc. The SC may include hardware elements (e.g., processors, internal communication buses, network interfaces, memory, and machine learning/AI processors). Some functions may be controlled with computer program instructions implemented as firmware or as software (e.g., computer program code stored on a non-transitory computer readable medium and executable by a processor).

In one embodiment the SC 305 controls the IoT system with an IoT machine learning (ML) and actuation module 309. It receives raw sensor data or HR events from the RNSP, determines how and when to respond, and sends the appropriate instructions back to sensors or actuators connected to the RNSP.

In one embodiment, the same functions are performed with smart phones that belong to the senior; smart phones that belong to caregivers; and smart phones that belong to family members. For example, a caregiver's smartphone may also be used to monitor conversations while the CG is in the home of the senior.

The video cameras 321 that can be positioned throughout a senior's living area and placed to capture their activities of daily living. The raw video data can be converted to various HR events by computer vision techniques. For example, the computer vision techniques may utilize pattern recognition techniques to recognize HR events. Alternatively, artificial intelligence techniques may be used to train an AI engine to recognize specific HR events from the video data.

An example of HR events of interest includes the senior eating, sleeping, visiting the bathroom, talking with other people, receiving medication, etc. Face and activity recognition technologies can be applied to verify who is shown in the video and what they are doing. For example, "At 3:02 PM caregiver Margaret helped senior Pam to get out of bed and go to the bathroom." In some applications, individual sensors, such as video cameras, motion sensors, thermal sensors, and the voice assistant may be used to detect when a senior is sleeping. However, there are an increasing number of commercial product that track sleeps patterns.

In one embodiment, Voice assistants (VAs) 323 listen to conversations and act as intelligent assistants. VAs may, for example, be used to recognize words in speech. However, they can also be used to recognize speech patterns, voice stress; mental acuity; depression; interpersonal actions; emotional states or other mechanisms indicative of loneliness; and emotional tone. This information can be used in different ways to generate HR events. The VAs can also be used to identify the speech from individuals and the course of conversations.

In one embodiment, VAs 323 passively listen to conversations, recognize what is being said, output transcribed speech, and initiate two-way conversations between an on-site user of a VA and a user of a VA at another location or a smart phone user. Speaker identification technologies can determine who said what. For example, a variety of speaker identification technologies are based on pattern recognition technologies to process and store voice prints. Voice-to-text techniques allow requests, commands, or questions to be interpreted as HR events.

In one embodiment, the System Database 301 records every interaction in the system as well as the scheduling of CGs. Raw IoT sensor data as well as events detected in that data are stored in the System Database. This provides a comprehensive history of the IoT data produced by every senior, family member, and CG whose agency uses SC.

In one embodiment, the senior's phone 315 includes a smart phone application (SPA) specialized for the senior to aid the senior in providing feedback about their care.

In one embodiment, the SPA on the CG's phone 317 monitors what the CG does and records CG-related events. Arrival (clock-in) and departure (clock-out) at the senior's location are automatically determined by a combination of GPS and indoor location technologies. Audio, video, step counts, barometric pressure, accelerometer readings, and other sensor data are all automatically gathered by the SPA while the CG on-site with the senior and off-site. Application and phone usage are recorded all the time, but especially when the CG is on-site with the senior. Aggregated information is reported at the end of each shift. For example, "Caregiver Margaret arrived at patient Pam's home at 8:00 AM and departed at 5:00 PM. Margaret walked 5466 steps, climbed 127 stairs, lifted 44 pounds. Margaret checked future shifts with the SPA for 12 minutes. She used Facebook for 3 hours 47 minutes, watched TV for 2 hours 12 minutes, talked with patient Pam for 8 minutes." Off-site HR events include a record of web sites related to home care, medical issues, and home care agencies other than those that currently employ the CG.

In some embodiments, the CG may also have a smart watch (SW) 335 accessible by the SPA of the CG's smartphone. A CG smart watch permits health readings of the CG (e.g., heart rate). In some embodiments, the CG SW is also a display for communication of alerts or other information from the SC. In some embodiments, the SPA of the CG's phone can access the same AD as the senior.

In one embodiment, the SPA on the family member's (FM's) phone 319 helps the FM provide feedback on the care of the senior.

In some embodiments, the system includes a social network monitor 329 that monitors information abound caregivers that is publicly available on social media. This may include social media postings by the caregiver. (e.g., a Twitter post by a CG "I hate my job caring for these old people—it sucks" or "I feel blessed that I can make a living helping take care of seniors"). A web browsing monitor 327 monitors the web browsing behavior of caregivers. This information, or portions thereof, may be stored in the system database 301 along with other information collected by the system.

Information from an Applicant Tracking System 325 or other employment database may also be provided to the system database.

In one embodiment, a caregiver predictive analytics unit 302 includes a machine learning system to analyze data stored in the system database and generate business intelligence information indicative of a likelihood that a caregiver will attrit (verb form of attrition). An action execution module generates suggested actions. A user interface module generates a user interface.

Figure 4:
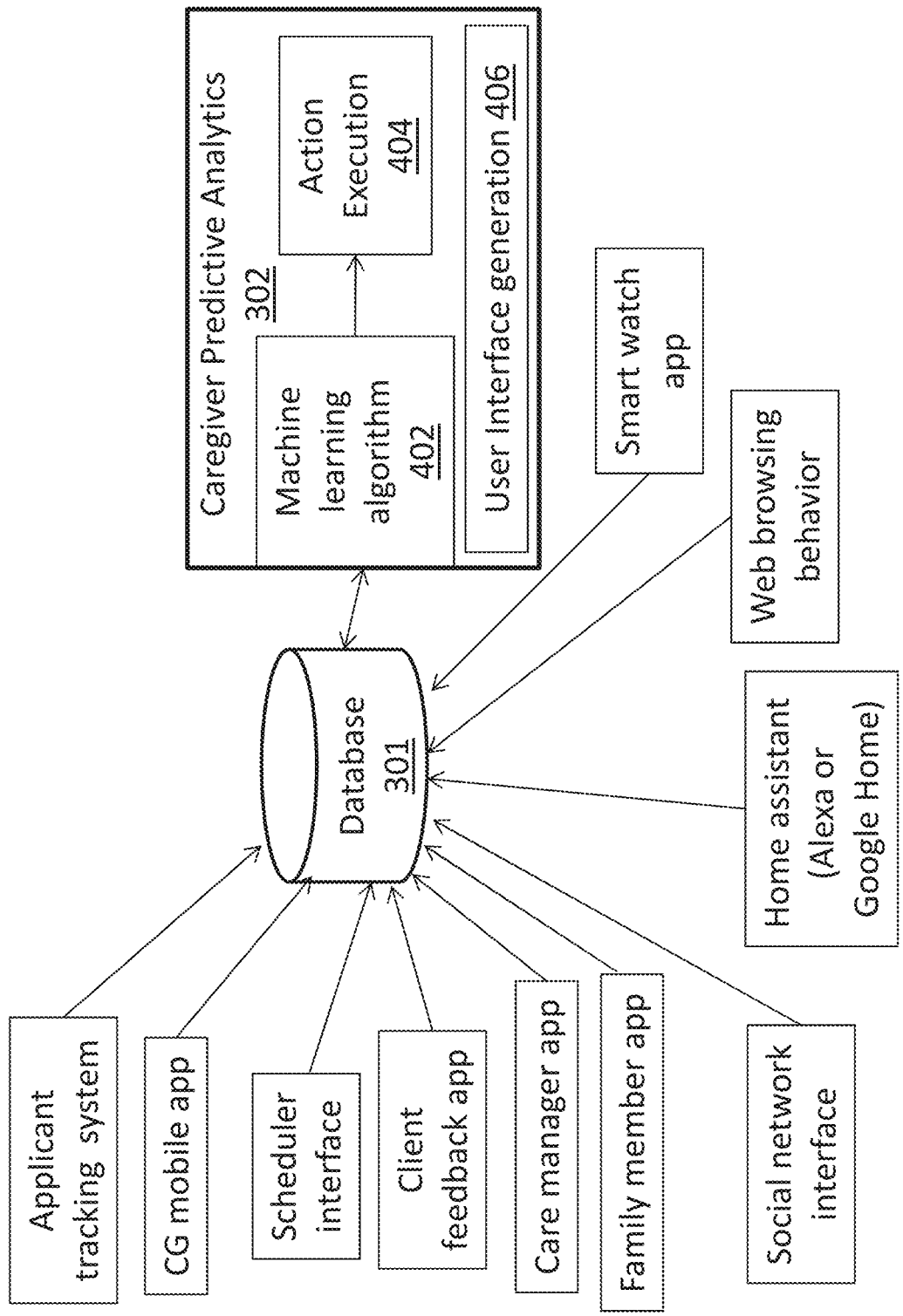
FIG. 4 illustrates an example of a portion of the system of FIG. 3 associated with predicting caregiver attrition in accordance with an embodiment.

FIG. 4 shows in more detail aspects of the caregiver predictive analytics unit 302. In one embodiment, it includes a machine learning system having a machine learning algorithm 402 and an action execution module 404 and may include a user interface generation module 406 to generate graphical signals based on caregiver risk attrition. As illustrated in FIG. 4, a variety of devices, modules and applications provide data that's stored in database 301 over time. The data characterizes various aspects of the interactions between the parties shown in FIG. 1 and is used by a machine learning (ML) system's algorithm to determine when caregivers are likely to attrit. An action execution module 404 determines which action to take, based on the results of the ML analysis, and can include controlling peripheral devices or networked applications.

Figure 5:
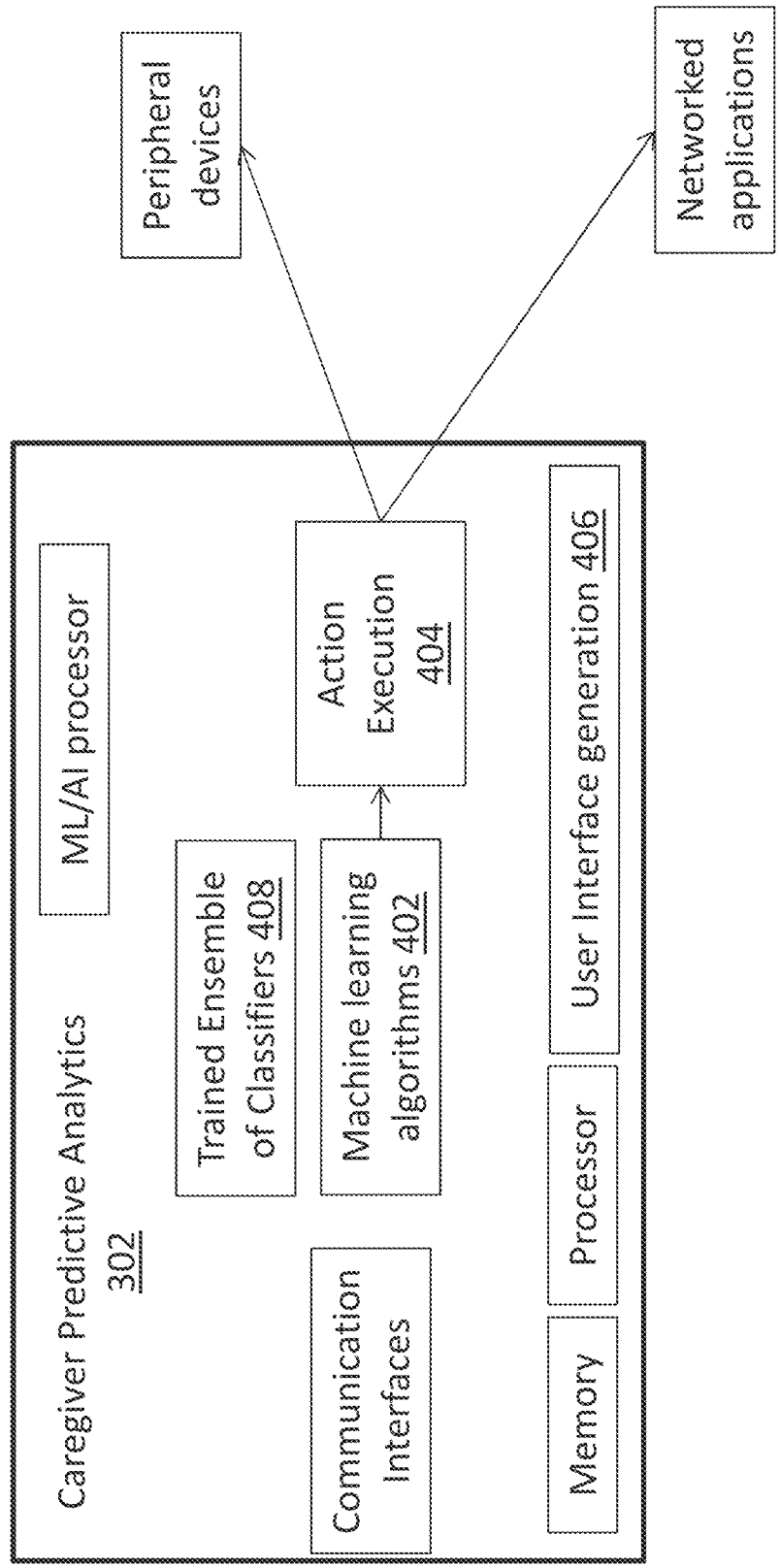
FIG. 5 illustrates in more detail an example of a machine learning system to predict caregiver attrition in accordance with an embodiment.

As illustrated in FIG. 5, the caregiver predictive analytics unit 302 may be implemented via a combination of hardware, processors, special purpose machine learning/AI processors, memory, firmware, software, internal communication buses, external communication interfaces, and network adapters. In one embodiment an ensemble of trained classifiers 408 is generated during a training phase and stored for use in making prediction. The trained classifiers 408 and the machine learning algorithms may be stored as computer program instructions on a memory of the caregiver predictive analytics unit 302 for execution on process. However, in one embodiment, a special-purpose machine-learning and AI processor is employed.

In one embodiment, examples of modules that provide input data include the following.
1. Applicant tracking system (ATS)—The ATS receives resumes, job applications, and interview results. It exchanges messages (emails or texts) with potential new hires. It stores information about CNA license number, CA Home Care Aid Registry number, CPR expiration date, country of origin, how long-ago applicants or their family members immigrated to the U.S., whether applicants are currently working or have ever worked at more than one agency simultaneously, the applicants' on-time performance to interviews, and the results of a personality test designed for caregivers.

In one embodiment, the output of the ATS is stored in key-value n-grams indexed by a unique identifier for the caregiver. For example, (CG 345, CNA license number, CA452377), (CG 345, CPR expiration date, Dec. 31, 2019), (CG 345, number of other home care agencies currently employed with, 2), (CG 345, interview 1, Feb. 7, 2018, "on time"), (CG 345, interview 2, Feb. 13, 2018, "10 mins. late"), (CG 345, on-boarding session, Feb. 19, 2018, "30 mins. late"), (CG 345, interviewer comments, "Martha says she dreams of doing home care but she doesn't maintain eye contact and was disrespectful to the agency owner").

2. Caregiver's (CG's) mobile app (CGA) or smart phone app (SPA). In one embodiment, the CGA is an application that runs on the caregiver's smart phone or in a web browser on their PC. CGs schedule and provide feedback about shifts, and comment on their personal situation with the CGA.

FIG. 6A shows an example of some of the feedback a caregiver provides about a particular shift. This includes whether they believe the client was satisfied, a description of any incidents that might have occurred on the shift, how many hours they would like to work next week, and whether, in general, they feel appreciated by both the client and the agency. Additional fields are included that allow the CG to comment on issues in their personal life, such as "I plan to move out of town next month" or "my mother's illness is getting worse." CGs can optionally be required to provide this feedback in order to be paid for a shift.

The questions asked in the Job feedback section of the CGA can be changed as needed to measure characteristics of the caregiver that might be relevant to their potential for attrition. The output of the CGA is stored in key-value n-grams indexed by a unique identifier for the caregiver, as described above for the ATS.

3. FIG. 6B shows an example of a scheduler interface, that may be implemented as a mobile device or desktop interface. In one embodiment, the SI is part of the system desktop interface that allows the Scheduler to enter qualitative information about the CG's performance and information received from the CG or other sources that might affect the attrition of the CG. Examples include questions with a fixed number of possible responses, such as Has Martha's attitude become worse recently? Yes or No, or free text comments such as "Describe anything that might affect Martha's chance of staying with the agency." This could be answered: "Martha's mother in Georgia is sick." Schedulers could optionally be required to provide this feedback to be paid for their work.

In one embodiment, the output from the SI is stored in key-value n-grams indexed by a unique identifier for the caregiver, as described above for the ATS.

Figure 6C:
FIG. 6C illustrates an example of a client job feedback app in accordance with an embodiment.
Figure 7:
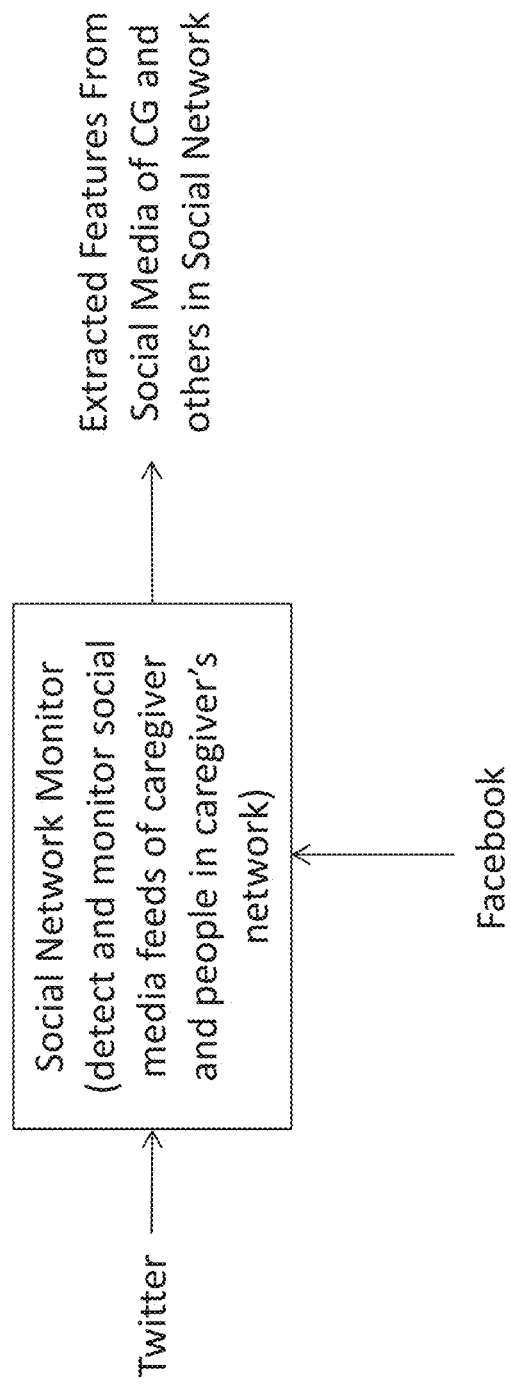
FIG. 7 illustrates an example of a social network monitor in accordance with an embodiment.

4. FIG. 6C shows an example of a client feedback app (CFA), which may also be implemented as a SPA. In one embodiment, the CFA is an application that runs on the client's smart phone or in a web browser on their PC. Clients enter information about their interaction with the CG. This includes questions with a fixed number of possible responses, such as "were you pleased with the service provided by the CG on your last shift? Yes or No." Another example is "Rate your CG on a scale of one to ten where one is 'replace this CG ASAP,' five is 'I'm fine with this CG but could try another one,'" or ten is 'I love this CG, do anything necessary to retain her.'" In one implementation, questions are included that can be answered with free text such as "Describe any problems that happened on the last shift" that might be answered "Jane didn't give me my medicine on time."

In one embodiment, both positive and negative comments are captured since a significant risk for attrition is happy clients hiring CGs away from their agencies. This is known as "going private pay." Negative comments such as the CG yells at me, the CG forgot to give me medicine could also indicate increased risk of the CG being terminated.

In one embodiment, the output from the CFA is stored in key-value n-grams indexed by a unique identifier for the caregiver, as described above for the ATS.

5. FIG. 6D shows an example of a care manager app (CMA). In one embodiment, the CMA is an application that runs on the care manager's smart phone or in a web browser on their PC. Care managers enter information about their interaction with the CG in the CMA. This includes questions with a fixed number of possible responses such as "Has the CG made any mistakes administering medication in the last five days? Yes or No." Qualitative evaluations are included such as scheduling issues (CG is often late), CG is not good match for the client, CG says she plans to move soon or CG's family member is seriously ill. Care managers could optionally be required to provide this feedback to be paid for their work.

In one embodiment, the output from the CMA is stored in key-value n-grams indexed by a unique identifier for the caregiver, as described above for the ATS.

6. FIG. 6E shows an example of a Family member app (FMA). In one embodiment, the FMA is an application that runs on the family member's smart phone or in a web browser on their PC. Family members enter information about their interaction with the CG as well as that of their loved one's interaction with the CG. Questions with a fixed number of responses and free text entries are allowed. These include comments about the attentiveness of the CG, the CG's on-time performance, and the overall level of satisfaction of the family member and the client with the CG. Complaints about hourly cost are captured here, such as it's getting difficult for our family to afford the CG.

In one embodiment, output from the FMA is stored in key-value n-grams indexed by a unique identifier for the caregiver, as described above for the ATS.

7. Social network monitor (SNM) to monitor social network feeds (e.g., Facebook, LinkedIn, Instagram, Twitter, etc.) In one embodiment, the SNM monitors the social network feeds of the CG, the client, and family members, for comments about the CG but also comments that might indicate the CG is likely to quit soon such as "Mom is seriously ill, I might be coming back to Georgia soon," or photos that show foreign locales the CG is planning to visit. Comments from the client and family members may also be monitored for signs that the family loves the work of the CG so much that they are contemplating employing the CG as private pay. For example, a family member might post on social media, "Mom is doing great with her new caregiver. We hope to hire the caregiver full time to take care of Mom as soon as we can."

Additionally, the social media feeds may be monitored for a general indication of the mood or psychological state of the CG based on a statistical analysis of the use of specific words used by the CG, phrases, and patterns of words. For example, the number of positive (upbeat) words or phrases may be compared with the number of negative (downbeat) words or phrases.

The monitoring may also include monitoring for words or phrases indicative of whether or not the CG likes taking care of seniors, such as a social media posting "My job sucks" or "I love my job." Additionally, in one embodiment, patterns of friending behavior are also monitored. Names of friends and their places of employment are recorded, especially if they are individuals with an elderly family member in need of home care or are supervisors at other home care agencies.

The social network monitor may, for example, be implemented as computer program instructions that searches/crawls the web for social media feeds associated with the name and demographics data of the CG. For example, in the case of a common name ("Sue Smith") employment data on the CG's location or an employment photo may be used to identify the correct social media links for the CG. In some embodiments, the social network monitor also searches and crawls for social media feeds of people in the caregiver's social network for additional information about the CG. As previously discussed, in some embodiments, the social media feeds of the client or family members may be search and the social media feed analyzed for information about the work performance and work satisfaction of the caregiver.

The Social Network Monitor may perform periodic or scheduled analysis of social media feeds (e.g., once a week) or on demand, depending on implementation details.

In one embodiment, the output from the SNM is stored in key-value n-grams indexed by a unique identifier for the caregiver, as described above for the ATS.

Figure 8:
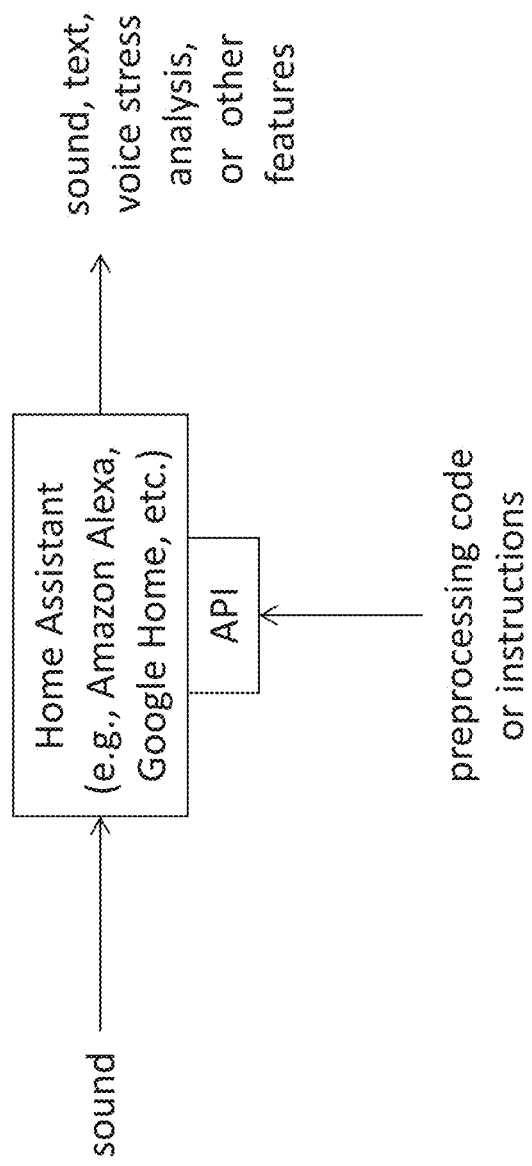
FIG. 8 illustrates an example of a home assistant application in accordance with an embodiment.

8. Home assistant (HA) applications. In one embodiment, the HA (see FIG. 8) is a device that deployed in the client's living space. It includes a microphone that constantly listens to the sound it hears and in its simplest form sends the sound to a data pre-processing module that applies speech recognition. That text is matched against previously stored phrase: action templates. A successful match triggers the associated action. For example, if a client says "Martha, you did a great job," the "great job" updates the client's satisfaction score for the CG.

Alternatively, the HA can perform the speech recognition and send the output text to the pre-processing module where the same phrase: action mappings are applied. In another alternative, sound preprocessing is applied that detects vocal stress (calm, slightly agitated, yelling) and identifies speakers. The participants in each conversation, its length, and the vocal stress of each speaker are recorded. This processing could occur on the pre-processing module on the server or on the HA itself. Preprocessing on the HA can optionally be enabled by custom code that's uploaded to the HA through an API. Speech recognition on the HA can be enhanced keywords or phrase: action instructions that are uploaded through the API.

Additionally, a voice stress analysis may be performed by the VA for the caregiver, the senior, or both. As is well known, various characteristics of the human voice tend to change when people are under stress. The voice stress analysis may be combined with other information such as words or phrases indicative of stress (e.g., swear words), or biometric data (e.g. pulse data from a smart watch).

In one embodiment, the output from the HA is stored in key-value n-grams indexed by a unique identifier for the caregiver, as described above for the ATS.

Figure 9:
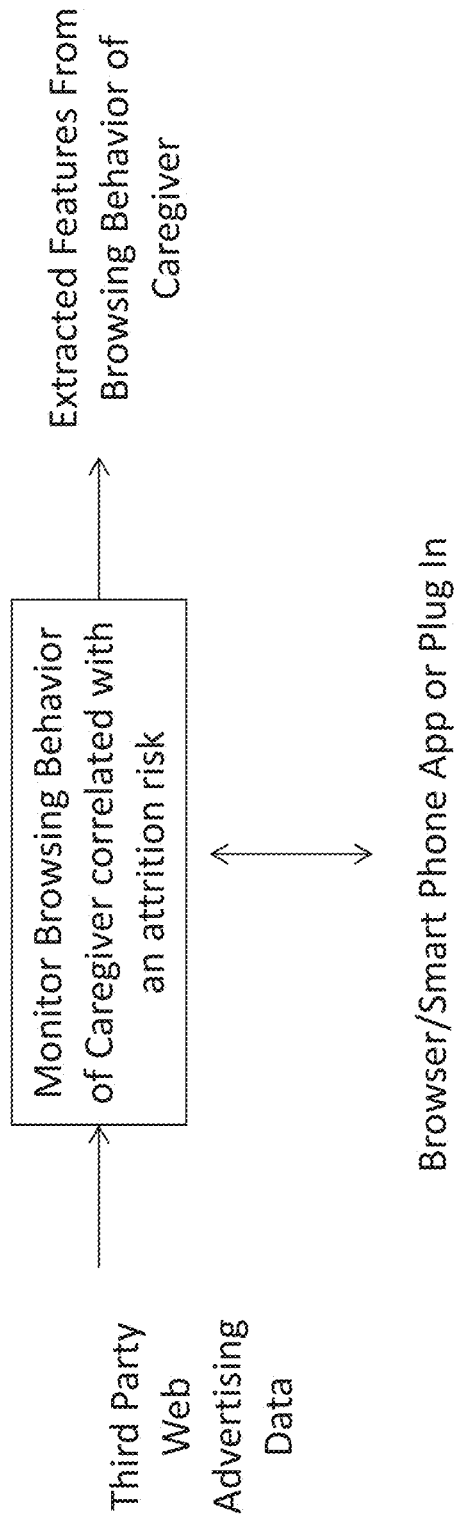
FIG. 9 illustrates an example of a web browsing monitor in accordance with an embodiment.

9. Web browsing monitor (WBM). Referring to FIG. 9, in one embodiment, the web browsing monitor (WBM)

receives information about the web sites browsed by the CG. This includes the URLs for the sites that were visited as well as the associated access times and IP addresses. In one embodiment, the information is provided by a browser plug-in that is installed on the CG's phone and/or PC when they enroll with an agency. The use of a browser plug-in should be implemented in a manner consistent with employment laws and legal privacy protections. For example, installation of the plug-in might be made in exchange for a rebate, a free phone, a free phone plan, or some other incentive. Moreover, one or more layers of privacy protection may be included to protect sensitive personal information of the CG not relevant to determining an attrition risk (e.g., ignoring browsing behavior of the CG not relevant to attrition risk, such as not monitoring visits by the CG to political sites, religious sites, atheist sites, etc.).

Alternatively, the WBM receives information about sites browsed from a web advertising service that is an intermediary between search engines and web advertisers (e.g., kismet.com, formerly Rocket Fuel). These services receive a URL request from a search engine that a user clicked on and within milliseconds reply with a bid for the advertising space on the web page the user will see. They maintain a history of the web sites browsed at given IP addresses and use this to predict the advertisements that users are more likely to click on, thus increasing the amount of money bid for those ads. The WBM receives the record of sites browsed by CGs (or clients) at given IP addresses (supplied at registration time or by the CG mobile app).

In one embodiment, a determination is made whether CGs are looking at the sites of other agencies, travel sites, or have recently booked tickets for out of town travel. These are all behaviors that are known to be predictive of attrition.

In one embodiment, the output from the WBM is stored in key-value n-grams indexed by a unique identifier for the caregiver, as described above for the ATS.

10. Smart Watch (SW) application. In one embodiment, SW applications (SWA are run on either the CG's or the client's SW (e.g., Apple iWatch). The SWA includes one or more microphones as well as sensors for one or more of: heart rate, blood pressure, blood glucose, body temperature, room temperature, respiration, swallow reflex, motion (accelerometer and directional gyroscope), camera, light level, location (Wi-Fi pings), barometric pressure, and whatever other sensors are provided in the SW.

In one embodiment, output devices on the SWA include a video screen, a buzzer, a speaker, and a heater.

One aspect of a smart watch is that its sensors can record motion information for the CG. A CG who is moving in a lethargic way may be bored or lazy, and thus be a potential attrition risk. Additionally, the sensors of a SW permit biometric data to be collected during a shift. If the CG's pulse rises when the senior yells at them, it may be a sign that the CG easily gets stressed when a senior is upset. Also, information on pulse rate of the CG may be correlated with a voice stress analysis of the CG performed by the VA.

Figure 10:
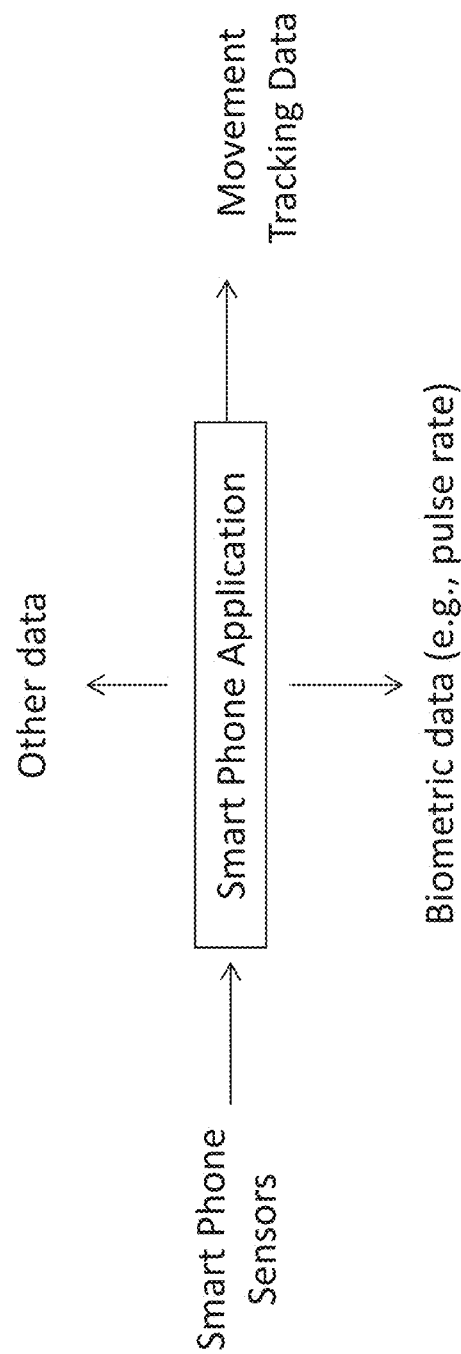
FIG. 10 illustrates an example of a smart phone module in accordance with an embodiment.

As illustrated in FIG. 10, in one embodiment the SWA receives smart phone sensor data and outputs data relevant to determining an attrition risk. As examples, this may include biometric data, such as pulse rate or movement tracking data. However, more generally, it may include other outputs derived from the sensor data.

In one embodiment, output from the SWA is stored in key-value n-grams indexed by a unique identifier for the caregiver, as described above for the ATS.

It should be noted that the above-described list is not necessarily required in a particular application. For example, the SW might be eliminated in some use applications. Other sources of data could also be omitted. However, supplying the database with data from many different sources provides a richer and broader source of data for a machine learning algorithm. Machine Learning for Attrition Risk Prediction In one embodiment, the machine learning system has a machine learning algorithm that computes a probability that a given caregiver, who has worked for N weeks, will attrit in the next M weeks (4 weeks is a commonly used value for M). The parameterization based on time worked to date is important because studies by the inventors of the present application indicate that the attrition of caregivers is highly time-dependent, particularly for new caregivers.

As time goes on (i.e., weeks, months, or years of caregiving), the attrition rate for a caregiver initially decreases. Some early attrition is inevitable in the sense of people quitting who are not suited to be caregivers. However, it is undesirable to have a high rate of attrition of people who achieved a minimum level of experience and are otherwise qualified and capable of being caregivers. It is thus valuable to identify which caregivers are at risk for attrition for planning purposes. If an agency has, say 100 caregivers and 20 of them are likely to attrit within one month then the agency may want to increase its recruiting efforts. Additionally, predicting attrition risks permits interventions before caregivers quit, such as offering stress management courses, pep talks or other moral boosters, pay raises, more hours, bonuses, etc.

Studies by the inventors of the present application revealed that caregiver attrition is surprisingly complicated in the sense of being dependent on many different variables. For example, the inventors began by first analyzing the quantitative data about caregiver performance such as the time when they show up for work every day versus the time when they were supposed to show up. A trend of increasingly showing up late was thought to indicate a declining interest in the job by the caregiver and a growing likelihood that they will attrit soon. Similar variables include the time when they were supposed to leave versus the time when they actually left, the lengths of the shifts they work, the time between shifts, the hours they work per week (utilization), and the number of unique patients they saw in the previous seven days. These are all measured relatively easily and are plausible indicators of a change in attrition risk.

However, analysis of a large number of real life cases of caregiver attrition showed that while some of their behavior might be reflected in the above statistics, caregivers act in more complicated ways. On the surface, they may seem happy with their work and their seniors are pleased, and then out of the blue they quit. Upon further review, based on interviews with the caregivers' managers, the inventors discovered that some typical reasons caregivers quit include the following:

1. "Caregiver wanted 8 AM to 4 PM w/in 5 miles of her house and quit when she couldn't get it,"
2. "Was lazy and became unreliable over time,"
3. "Her last client was a young person who died after a long illness, she needed some time away from care giving,"
4. "Got older and couldn't accept the clients she was offered because they often needed physical assistance she was incapable of providing,"

5. "Became annoyed with her client and started canceling shifts,"
   6. "Refused to do training and eventually left caregiving altogether,"
   7. "Got an offer for increased salary elsewhere."

These reasons for quitting, among others, are represented by data captured from the applications shown in FIG. 3 or 4. Following the above examples:
   1. The caregiver mobile app (see FIG. 6) captures feedback from the caregiver about their perception of the client's happiness with their performance as well as their preferences for future work, including the number of hours they'd like to work and the maximum distance they'd like to commute.
   2. The client feedback application allows the client to input comments about the caregiver from a fixed list of alternatives, including attitude on the previous shift. These include "happy," "competent," and "attentive," as well as "lazy," "unreliable," and "slept."
   3. The care manager app allows for the entry of information about the condition of the client, including, "at home and healthy," "hospitalized," and "in hospice," among others.
   4. The scheduler app allows for the entry of information about the reasons why caregivers refuse shifts. Examples include "no transportation," "parents visiting," and "can't lift that client."
   5. The home assistant app (see FIG. 8) monitors the conversations between caregivers and patients and, based on analysis of the stress in the caregiver's and client's voices, or the words exchanged, e.g., "Martha, I want my medication NOW not five minutes from now!"
   6. The social network interface monitors the caregiver's postings and detects satisfaction with the caregiving profession. For example, postings like "my patient is really nice to me" reflect positively and postings like "this job sucks" indicate a propensity to quit.
   7. The receipt of an offer for increased salary is one of the most significant reasons why caregivers quit. We can capture indications about this from all the applications in FIG. 3 but especially the social network interface, home assistant application, and web browsing behavior. Comments on social networks like "Woohoo, I got a better offer" are sure signs the caregiver is at risk for attrition. A home assistant in the client's and/or caregiver's home might pick up similar comments. Web browsing of sites for other agencies besides the caregiver's current employer are also signs that the caregiver might be looking for more money or has already received a better offer.

Note that using many different types of information provides a much richer source of information about the CG for a machine learning system to make predictions. For example, in the different examples of FIG. 6, obtaining feedback from different sources gives a more accurate understanding of Caregiver Martha. Her own job feedback may differ from that of the client, her manager, the scheduler, and family members of the client. She could be doing her job at a very high level but be frustrated she is being chewed out by a senior with an attitude problem. Supplementing the feedback data with biometric data from a smart watch might reveal that Martha's pulse rises when she enters the home of a senior who regularly chews her out. Other data, such as from the VA, may also reveal signs of Martha's voice stress as she is being yelled at for doing her job of helping the senior exercise and eat right. Adding more data sources, such as social media feed data, may also reveal aspects of Martha's state of mind, such as if she complains in her posts about having a client from hell. Data on the number of hours and number of clients Martha has may be another important source of information. For example, Martha may be working only 20 hours a week for just one difficult client and feel frustrated that she is not making enough money in addition to other considerations. Another piece of data, such as Martha browsing the website of a competing agency or planning a trip may provide yet another clue that Martha is at risk for quitting. Knowing how long Martha has worked as a CG may provide more clues. For example, if Martha is still fairly new at being a CG she may not yet know how to manage stress from the job or not take comments from the senior personally.

In this example, Martha is a great CG such that early prediction of an attrition risk for Martha may be valuable to an agency to perform an intervention, such as praising Martha for her good work; offering a pay raise; offering Martha a stress management course or tips on how to deal with difficult clients, etc.

Machine Learning Types

Broadly speaking, a wide variety of machine learning or Artificial Intelligence (AI) techniques may be used for the attrition risk prediction. Data sets may be collected and used to generate training data. The machine learning or AI may also perform technique to adapt and learn over time after an initial training. However, as described below in more detail, various optimizations may also be performed that are directed to some of the special problems associated with caregiver attrition. One of these is caregiver behavior changes based on the length of time caregivers have worked. Seasoned caregivers are behaviorally different than novice caregivers.

Machine Learning Ensemble Training

Figure 11:
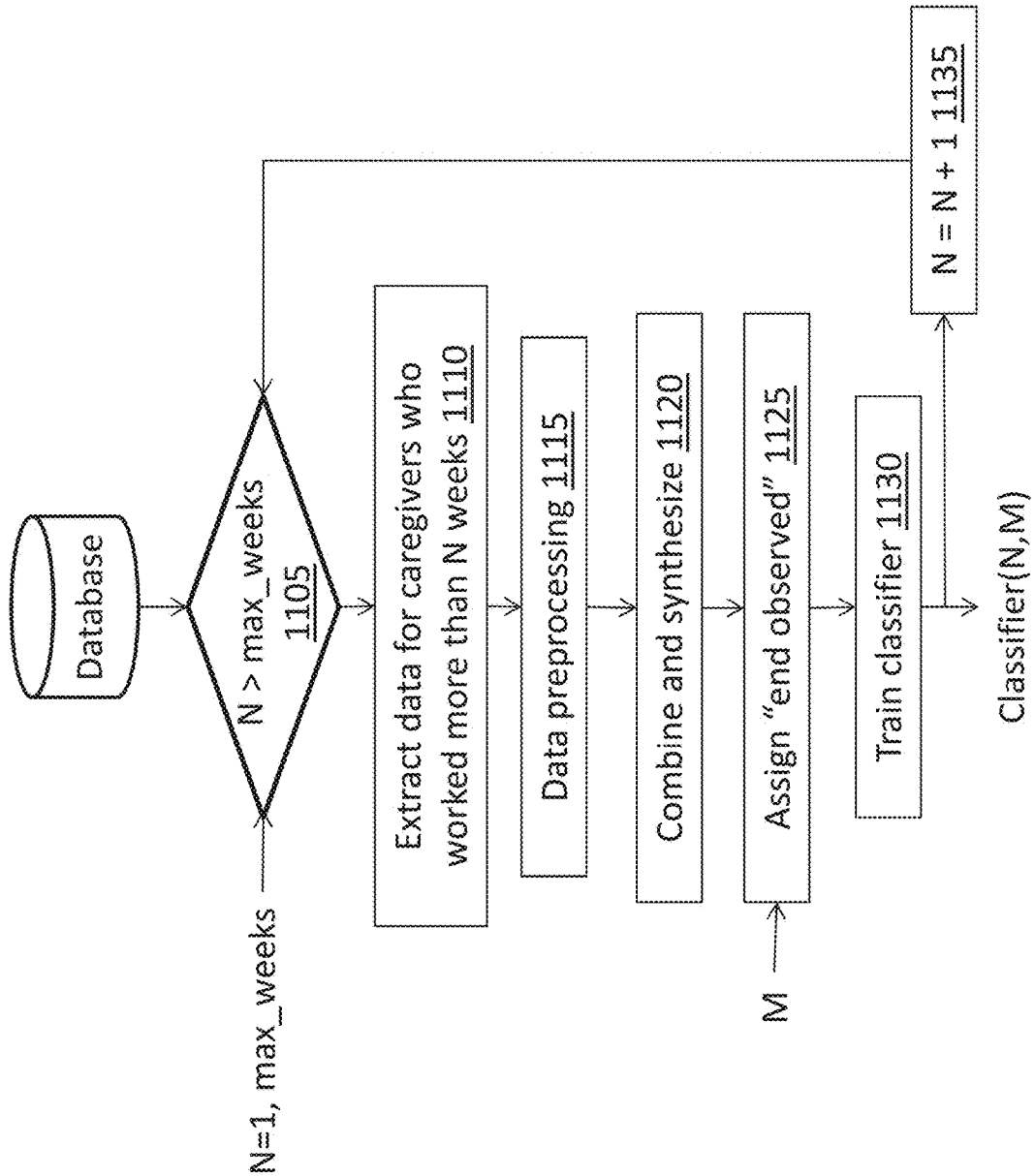
FIG. 11 illustrates a flowchart of machine learning ensemble training in accordance with an embodiment.

In one embodiment, caregiver attrition is predicted employing an ensemble of classifiers as illustrated in the flowchart of FIG. 11. As illustrated in diamond 1105, the process performs an iteration loop in which the process separately trains an ensemble of classifiers for different longevities (expressed as N weeks). This models the time-varying behavior of a caregiver's decision-making process, as we observed in the field. For example, caregivers who do well over time are at an increased chance of getting a better salary elsewhere.

This method of claim 11 gives us hundreds of classifiers (208 for four years of caregiver history), each of which models the preceding N weeks of caregiver performance. Then, given a caregiver who has successfully completed N weeks of employment, we select the classifier that was previously trained on caregivers who worked for more than N weeks and use it to predict the probability that the caregiver will attrit in the next M weeks.

This technique is an alternative to using a conventional method such as survival analysis with Cox proportional hazards and time varying covariates. Those methods are suitable for describing general survival characteristics of a population. In contrast, our ensemble strategy is easily customized to a population of caregivers and it is ideally suited for making predictions about the short-term future of individual caregivers, which is precisely what we need.

In block 1110, the process extracts all the data in the database that have been accumulated for caregivers who worked more than N weeks. In one embodiment, this includes raw data from all the sources shown in FIG. 3-4.

In block 1115, a data preprocessing step is given numeric features, categorical variables, and free text input. It applies various transformations to produce numeric feature vectors that contain binary or real values. These feature vectors are suitable for machine learning algorithms.

In one embodiment, a skew of numeric features, such as the age of the caregiver, is evaluated and if its absolute value is greater than one, a log transformation is applied. This makes highly skewed distributions less skewed and their distributions more normal.

One hot encoding is applied to categorical variables, such as the list of possible answers to questions in the caregiver mobile application (CMA). It converts those categories to labels and the value of the features to bits, with a one bit indicating the presence of the label and zero its absence.

The sentiment of free text input, such as the comments about a caregiver that are typed by a senior, uses an unsupervised learning algorithm that assigns a category (GOOD or BAD) to the comment [See Turney, P. D. 2002. "Thumbs up or thumbs down? Semantic orientation applied to unsupervised classification of reviews." In Proceedings of the 40th annual meeting of the Association for Computational Linguistics, 417-424, the contents of which are hereby incorporated by reference]. In the first step, the part of speech (noun, adjective, adverb, etc.) of each word is determined and sequences of words (phrases) that contain adjectives or adverbs are identified. The second step estimates the semantic orientation (positive or negative) of each phrase with a pointwise mutual information (PMI) algorithm. A phrase with a positive semantic orientation indicates the senior is happy with the caregiver, e.g., "pleasant attitude." A negative semantic orientation is a red flag for bad behavior, e.g., "horrible service." The third step of the technique assigns a senior's entire comment to the GOOD or BAD class based on average semantic orientation of the phrases extracted from it. Numerically, GOOD is coded one and BAD is coded zero.

Block 1120 creates a single feature vector for each caregiver based on combining and synthesizing data. An example portion of a feature vector is shown below.

Example single feature vector: Caregiver id number, hiring date, gender, country of origin, citizenship, date of birth, number of weeks worked, number of client happy Yes ratings, number of client happy No ratings, Number of client happy U ratings, total GOOD caregiver incidents, total BAD caregiver incidents, number of hours CG wanted to work at week N, number of hours actually worked at week N+1, desired distance from home at week N, actual distance of clients from caregivers home at week N+1, number appreciate Yes ratings, number of appreciate No ratings, number of appreciate U ratings, etc.

In block 1125, each feature vector is assigned an "end observed" value that equals 1 if the corresponding caregiver attrited before the end of week N+M and equals 0 if the caregiver worked more than N+M weeks.

In block 1130, a classifier (N, M) is trained for the current longevity. In one embodiment he training data derived from the above process is used to train a logistic regression classifier that estimates the probability that a caregiver who's worked N weeks will attrit within the next M weeks.

Logistic regression is the preferred solution for each member of the ensemble of classifiers because it inherently provides a way to assess the significance of individual features and it computes a probability (e.g., a probability that a caregiver who worked N weeks will attrit within the next M weeks) that can be used to create the desired user interface. A deep learning (DL) classifier could also be used with the same feature vectors. DL can find more complex decision boundaries but needs a scaling procedure to convert its numeric output to a probability.

As illustrated in block 1135, the process is then iterated (N=N+1) to train the next classifier in the ensemble, with the process continuing until some maximum number is reached.

An experimental implementation uses the Logit method in the statsmodels package (http://www.statsmodels.org) in python. The features described above are the "X" data and the end_observed values for each feature vector are the "y" values. The Logit.fit( ) method fits a logistic regression to the features given the classifications for those vectors as expressed in their end_observed values.

An example summary of the fit for 21 features on 20,000 example feature vectors, edited for brevity, is shown below. The column P>|z| tells us whether the corresponding feature is statistically significant in making decisions. Values less than 0.05 tell us that the corresponding feature was significant at the 95% confidence level.

In the following example, we see that the age of a caregiver on the day they were hired was not statistically significant but the features depicted here (client_happy_Y, client_happy_N, client_happy_U, and good_CG_incidents) were all significant.

```
Optimization terminated successfully.
   Current function value: 0.436173
   Iterations 612
                        Logit Regression Results
```

| Dep. Variable: | end_observed | No. Observations: | 2000 |
|---|---|---|---|
| Model: | Logit | Df Residuals: | 1997 |
| Method: | MLE | Df Model: | 2 |
| Date: | Thu, 02 Aug 2018 | Pseudo R-squ.: | 0.370 |
| Time: | 14:11:04 | Log-Likelihood: | −87.23 |
| converged: | True | LL-Null: | −138.5 |
| | | LLR p-value: | 4.976e-2 |

| | coef | P>|z| |
|---|---|---|
| age_at_hire_date | −0.1006 | 0.301 |
| client_happy_yes | −0.6369 | 0.005 |
| client_happy_no | −0.3367 | 0.008 |
| client_happy_U | −0.4199 | 0.002 |
| good_CG_incidents | −0.2214 | 0.022 |
| ... | | |
| intercept | 7.0107 | 0.107 |

Figure 12:
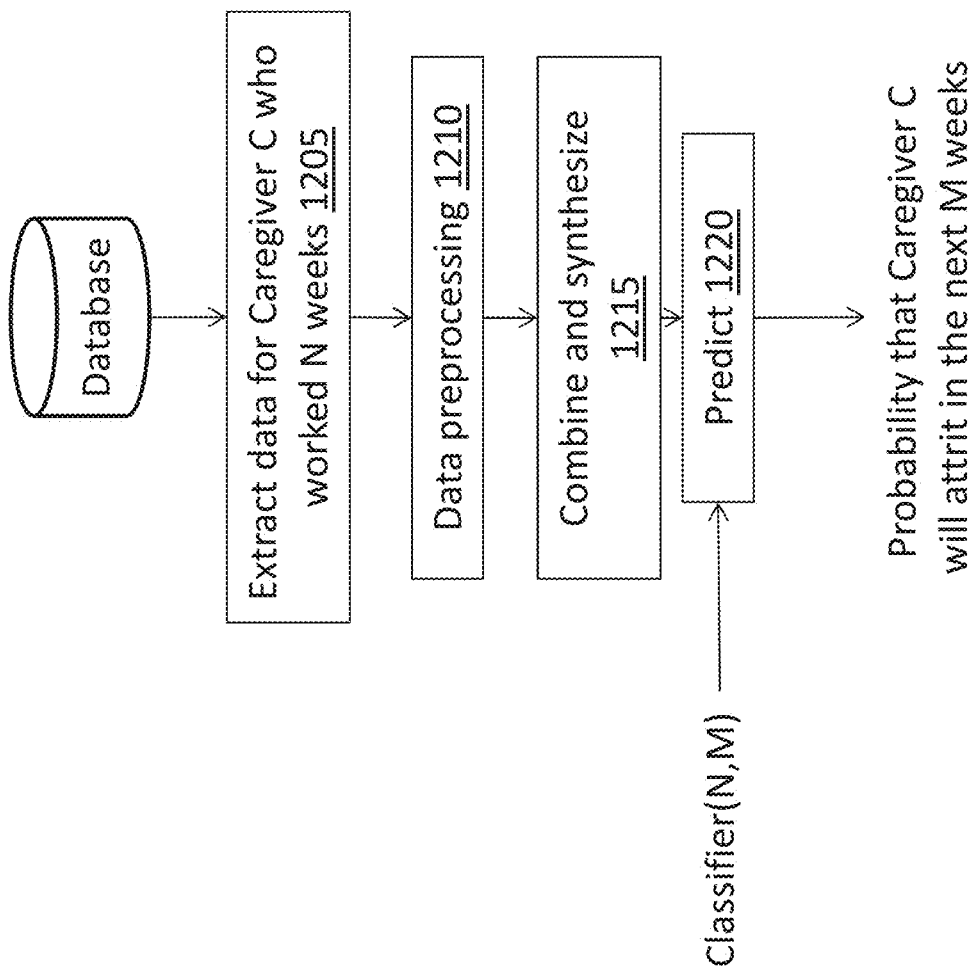
FIG. 12 illustrates a flowchart of machine learning prediction in accordance with an embodiment.

FIG. 12 is a flowchart showing a method of using the trained ensemble of classifiers. The machine learning prediction process computes the probability that a given caregiver (Caregiver C) who has worked N weeks will attrit within the next M weeks. All the data about Caregiver C is extracted from the database in block 1205 and input to a data preprocessing (block 1210) and combine and synthesize block (1215) that are similar or identical to those used for training. The result is a feature vector that is the same dimension as the feature vectors used for training. In block 1220 prediction is performed using the classifier (N,M) where N is the number of weeks Caregiver C has worked and M is the same number used in training. Application of the Logit.fit.predict( ) method to any feature vector returns the probability that Caregiver C will attrit in the next M weeks.

Figure 13:
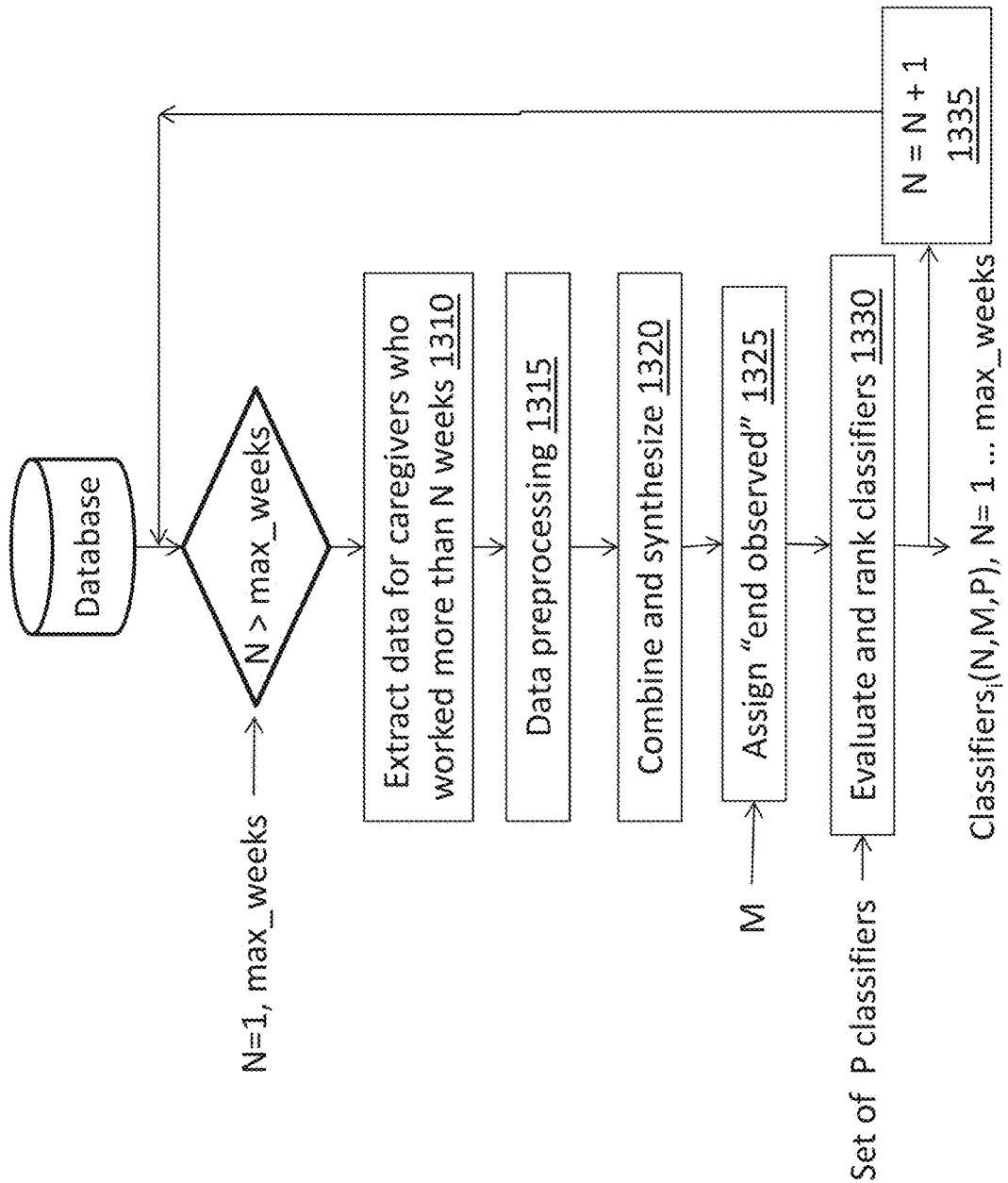
FIG. 13 illustrates a flowchart of population-adaptive classifier selection in accordance with an embodiment.

FIG. 13 is a flowchart illustrating a method of population adaptive classifier selection. Analysis of a large number of cases of caregiver attrition by the inventors indicated that caregivers use different strategies for making their decision about whether to quit depending on how long they have been employed. For example, we know that there is a high likelihood that caregivers will quit in their first 3 weeks of employment because of a difference between expectation and reality. They thought caregiving would be a good occupation but realized they did not like it once they had their first client. After that initial adjustment period, the decision-making process of caregivers changes. The caregivers by in large have embraced their occupation after about ten weeks on the job and increasingly base their decision about whether to stay on the job on external factors like the needs of their families or their own changing physical limitations.

This change in the way caregivers make their decisions, which is similar to the maturation process in humans as we move from childhood to adolescence to adulthood, implies that the underlying machine learning algorithm might need to change so that it reflects how caregivers make their decisions at any point in time. For example, during the first three weeks (N<=3), when caregivers are in their initial adjustment period, a decision tree classifier might be appropriate because the predominant decision criteria are straightforward (e.g., do I like caregiving, Yes or No). As time progresses, a multi-layer perceptron or deep learning method, that can infer complex decision boundaries in feature space, might better reflect how caregivers decide whether to continue working.

The issue would then be how to choose the classifier that best reflects how caregivers make their decisions at any point in time. FIG. 13 shows a population-adaptive classifier selection strategy that achieves this goal. The process loops over the same values of N (1 to max_weeks) and performs the same steps as before: extract the data for caregivers in block 1310, preprocess it in block 1315, combine and synthesize in block 1320 to generate a single feature vector, and assign the end_observed variable to each feature vector in block 1325. Then a set of P classifiers (e.g., that might include logistic regression, stochastic gradient descent, bagging, AdaBoost, Naïve Bayes, KNN, SVC, decision tree, random forest, gradient boosted regression trees, multi-layer perceptron, and deep learning) are passed to the evaluate and rank classifiers technique in block 1330.

The process of FIG. 13 assigns "goodness" value to each classifier in the set of P classifiers (its accuracy or F1 Beta score on a test set) and sorts the classifiers in decreasing order by that value. After completing the loop over all values of N, we have a two-dimensional list of classifiers. For each value of N we have a different list of classifiers ranked by how well they predict the attrition of the caregivers for the corresponding value of N.

Figure 14:
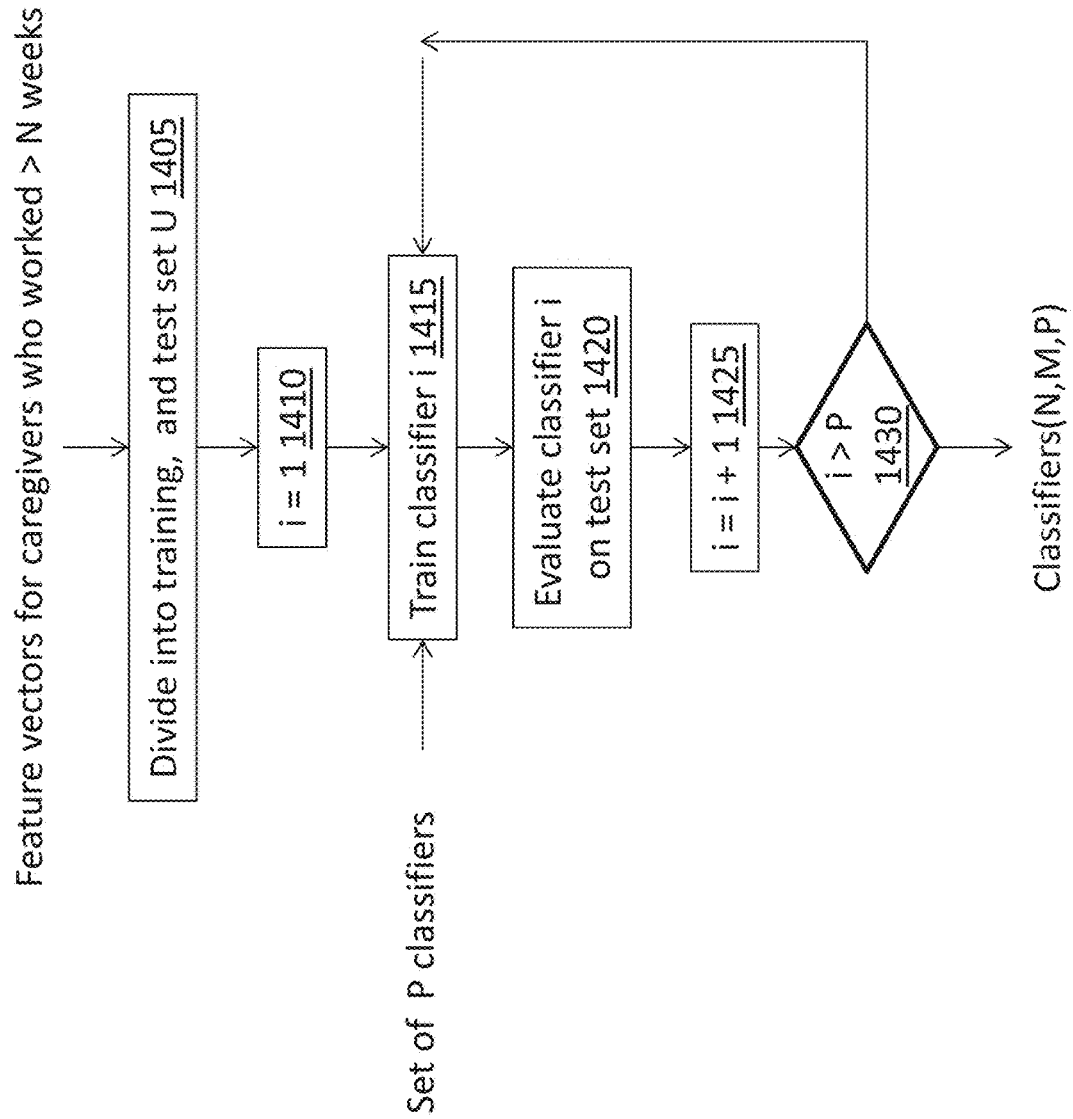
FIG. 14 illustrates a flowchart of evaluation and ranking of classifiers in accordance with an embodiment.

FIG. 14 is a flowchart showing a method to evaluate and rank the classifiers in block 1330. In block 1405, given set of feature vectors is divided into training and test data. Typically, we assign a random set of 80% of the feature vectors to the training data and 20% to the test data. Then we loop selected over each of the P given classifiers, starting with i=1 in block 1410, increasing i in block 1425 to i+1, and ending the looping if i>P in decision diamond 1430. In block 1415, we train each classifier on the training data and evaluate it on the test data in block 1420. Each test sample is assigned a decision (we predict whether or not the corresponding caregiver will attrit in the next M weeks). We compare our prediction to what the caregiver actually did. From these results we compute the number of true positives (TP), true negatives (TN), false positives (FP), false negatives (FN), Precision=TP/(TP+FP), and Recall=TP/(TP+FN).

In one embodiment, each classifier is assigned two scores: accuracy=(TP+TN)/(TP+TN+FP+FN), and F1 Beta score=2*Precision*Recall/(Precision+Recall). We rank the classifiers by either accuracy or F1 Beta score (determined by parameter setting) and return that ranked list. The effect is that the classifier that best models how caregivers make their decisions at a given point in time is at the top of the ranking. This is the classifier that is applied later when predicting who will attrit in week N.

In one embodiment, a user interface displays an indication of the risk of attrition for one or more caregivers. In principal this could be displayed as a number (e.g., 46%). However, in many applications a simple, easily understood user interface is critical for commercial success. In one embodiment, the risk of attrition is classified into a small number of different categories or classifications and each classification is represented graphically by a graphical element, such as a color, shape, or texture. For example, one option is two classifications (e.g., high/low). Another option is three classifications (e.g., high/medium/low). Other numbers of classifications are also possible (e.g., 4, 5, 6, etc.) such that there are two or more different classification options with each classification option represented graphically by a distinct attribute, such as by color, shape, or texture.

In one embodiment, there are three classifications represented by three different colors such as Green, Yellow, Red (GYR) with a GYR classifier that assigns one of three colors to each caregiver. A caregiver in the green group is considered to be at low risk for attrition in the next M weeks. A caregiver in the yellow group is at moderate risk and a caregiver in the red group is at high risk for attrition. These are caregivers that demand immediate attention and personal intervention by either the care manager, scheduler, or agency owner or manager if they would like to retain those employees. They might choose to praise them publicly, as this has been shown to be effective in improving retention, raise their salary, or listen to and address any personal concerns they might have.

Figure 15A:
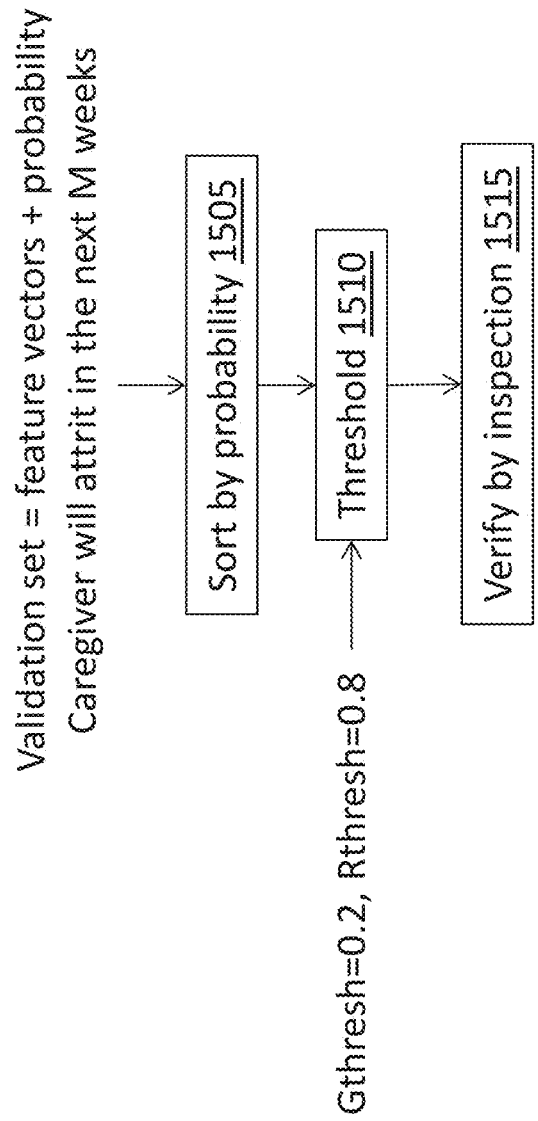
FIG. 15A illustrates an example of color classification of attrition risk in accordance with an embodiment.

FIG. 15A shows a Green, Yellow, Red classifier that uses the output of a logistic regression classifier (LRC). After training the LRC on a set of training data, we apply it to a different set of feature vectors and classes (the end-observed variable) called the validation data. The LRC returns a probability that the corresponding caregiver will attrit in the next M weeks. In block 1505 the feature vectors are sorted by that probability. In one embodiment, an adjustment is made of two thresholds in block 1510 (Gthresh for the Green level and Rthresh for the Red level). All the feature vectors below Gthresh are assigned "did no attrit" and those above Rthresh are assigned "attrited" as their result. In one embodiment a comparison is made of those decisions of the GYR classifier to the actual decisions of the caregivers.

Figure 15B:
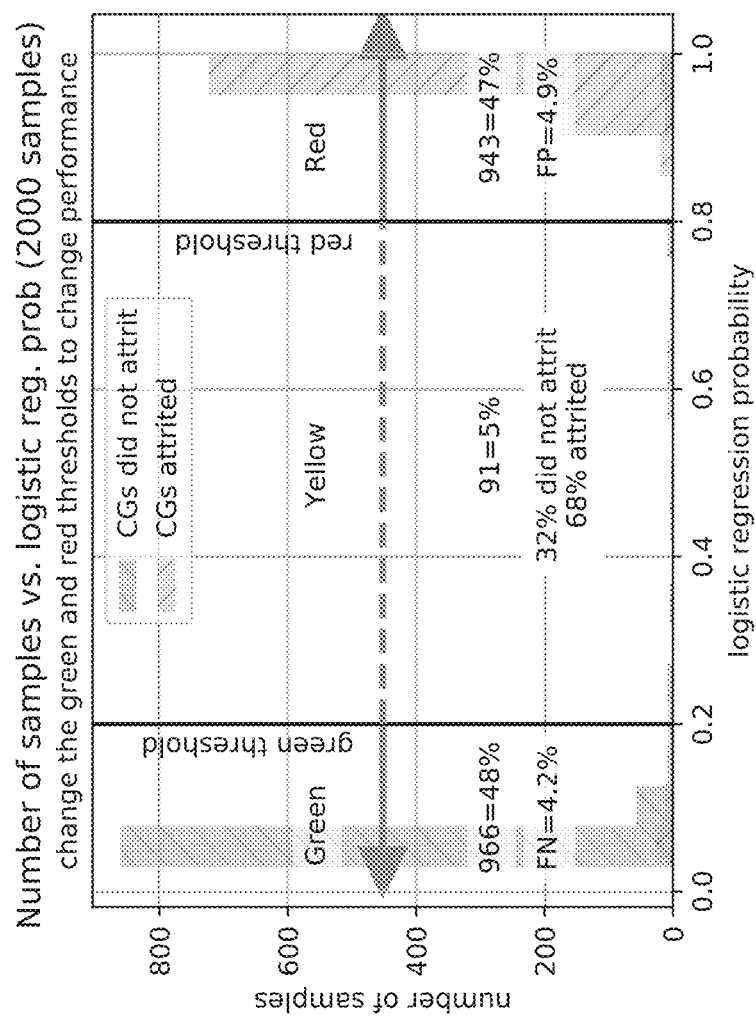
FIG. 15B illustrates an example graphical display of results of an example color classification in accordance with an embodiment.

In one embodiment, the number of true negatives, false negatives, true positives and false positives is computed and displayed graphically on a histogram of the number of caregivers vs. logistic regression probability as shown in FIG. 15B. In this example 48% of the caregivers (966 out of 2000 in the validation set) were "Green" and they in fact did not attrit. 4.2% were Green and did attrit. 5% of caregivers were "Yellow," indicating they were at increased risk for attrition and 68% of them actually did attrit in the next M weeks. In this example, 47% of caregivers were "Red" and 95.1% of them attrited in the next M weeks. The inspection of this graphical depiction verifies that the Gthresh and Rthresh values we chose do in fact provide a reasonable separation of the validation data into Green, Yellow, and Red groups. Henceforth, we apply the GYR classifier to the output of machine learning prediction to obtain green, yellow, and red signals for the user interfaces.

Figure 16:
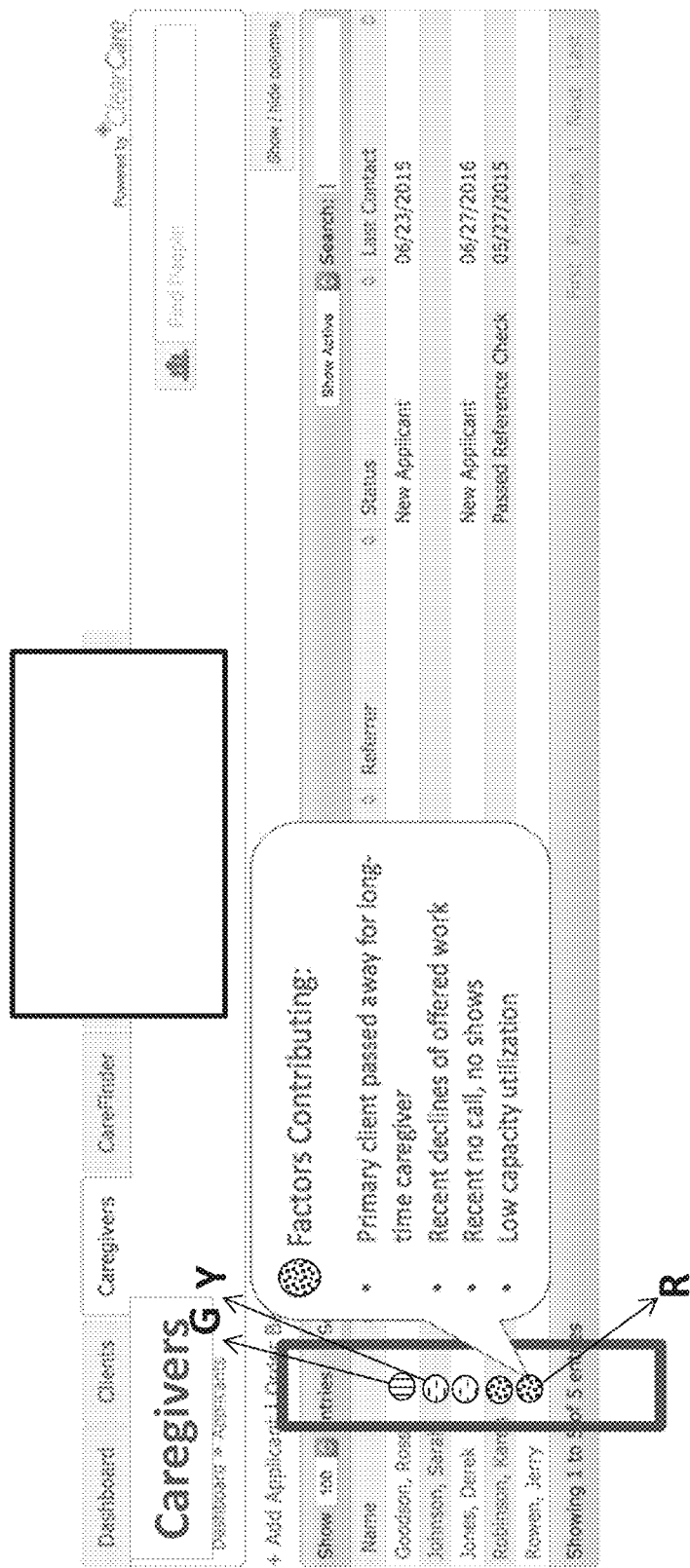
FIG. 16 illustrates an example of a scheduler user interface in accordance with an embodiment.

FIG. 16 shows an example of a Scheduler's user interface. A Scheduler is someone who inputs characteristics about a pending caregiving assignment and is provided a list of caregivers whose skill set, desires, and schedule constraints match that specification. The Scheduler then chooses who to assign that job. The embodiment of FIG. 16 adds valuable information to the Scheduler's user interface. The probabilities that each caregiver will attrit in the next M weeks are converted to green, yellow, or red colored circles that indicate varying probabilities of imminent attrition, as described above. The features contributing to that decision (computed as described below) are listed in a pop-up that is displayed when the user hovers their mouse over the colored circle. In this example, CG Jerry Rowen has a 95% chance of attriting in the next M weeks and the ranked features that contributed to that decision are that his primary client passed away, he recently started declining offered work, he recently started not calling back and not showing up, and the number of hours he's worked in the last week were significantly lower than the number of hours he wants to work weekly.

To determine the amount that each feature contributed to the decision about each caregiver mentioned above, the system loops over each feature in the caregiver's feature vector. We set each feature to its population mean, effectively neutralizing its influence on the decision, and apply the prediction function. The system notes the amount the probability changes. The larger the change, the more important the feature was in making the decision about the corresponding caregiver. The system then sorts the features in decreasing order by the amount they changed the overall decision probability. The features at the top of the list were most significant and are displayed in the Scheduler's user interface.

FIG. 17 shows an example of a user interface for Agency Owners or Managers that summarizes groups of caregivers who are at high risk of attrition in the next M, 2*M, and 3*M weeks (note: in one embodiment the number of periods and their extent is adjustable/configurable as needed). The objective is to signal whether the agency owner is at risk of a mass defection of caregivers in the near future that could be catastrophic to his business. These rankings are obtained by setting M to a series of values (e.g., 2*M, 3*M) and re-running the machine learning training and prediction procedures summarized in FIGS. 11-15. The GYR classifier is applied to all the caregivers and display those who are in either the G, Y, or R groups, as determined by user selection.

In the example shown in FIG. 17, two caregivers are at high risk for attrition in the next four weeks and three in the next eight weeks. This level of potential attrition could be considered normal by the agency owner or manager. He may or may not try and convince those caregivers to stay. However, 16 caregivers are at high risk for attrition by November 3 (12 weeks from today). This would be considered a disaster by the agency owner or manager as he would be losing 20% of his staff. This would greatly impact the operation of his company and could in fact affect its reputation and future viability since the agency would be unable to fulfill its current contracts and would need considerable time to recruit new staff. In response, the agency owner or manager could individually contact each caregiver and attempt to address their issues. He could hold a town hall style meeting and encourage open discussion about issues facing his caregivers and how the whole company could work together to address them. The message from this meeting about the agency owner's concern for his caregivers would reach those in the Red zone and others who might shortly become members of the Red zone group.

In some embodiments, a set of recommended retention/attrition risk-reduction action items is generated and displayed. For example, in addition to displaying factors regarding why a caregiver or group of caregivers has been assigned a particular classification, a set of action items may be suggested. For example, in the example of FIG. 17, a suggested action item of holding a company town hall meeting could be automatically suggested based on the risk a certain pre-selected percentage of the CG staff is likely to attrit within M weeks. The suggested action could be rule based. Alternatively, machine learning or AI techniques could be used to generate a suggested action item, from a set of action items, based on using data from previous interventions as training data. For example, a set of action items might be to issue company wide bonuses to all caregivers, bonuses to selected caregivers, mentoring to some individual caregivers, and so on.

Figure 18:
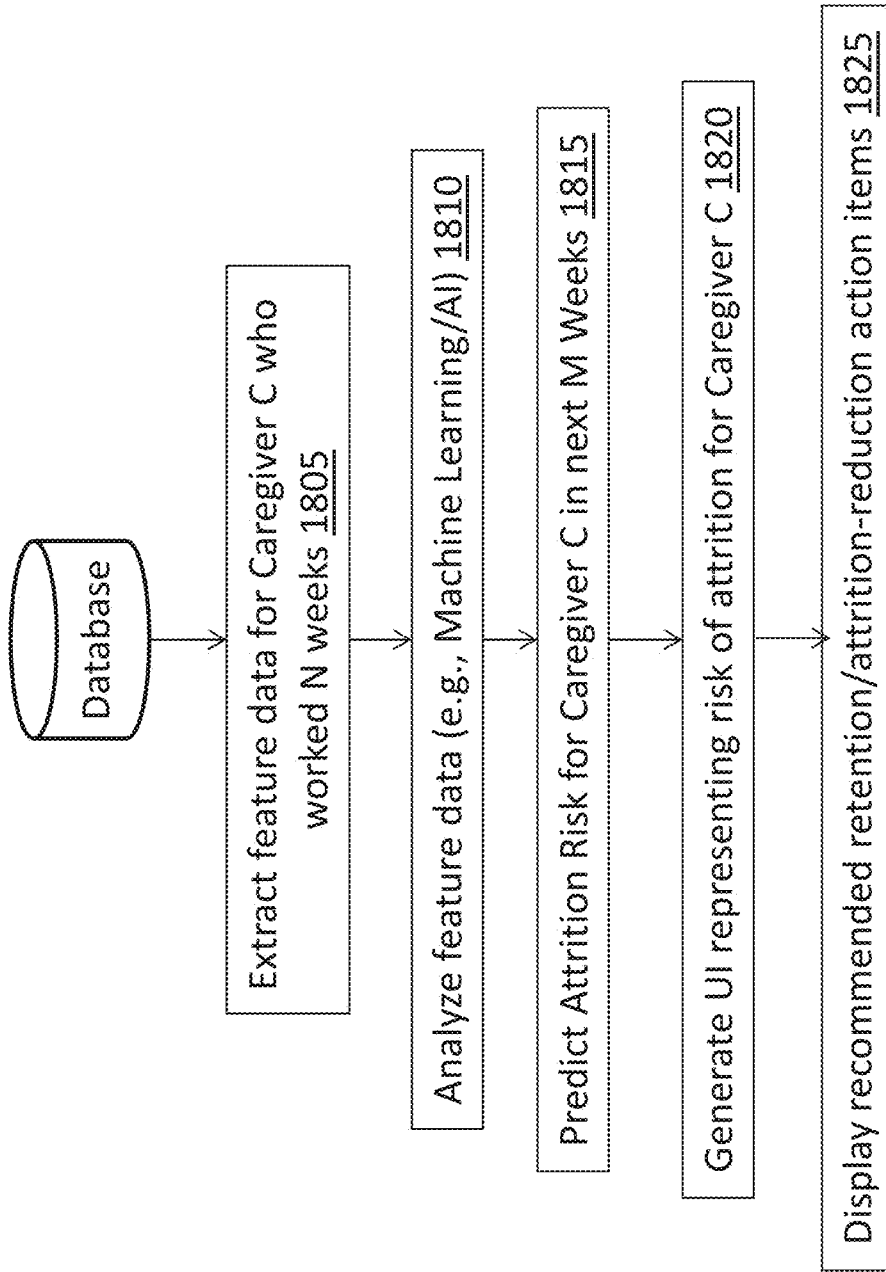
FIG. 18 is a flowchart of a method of generating a user interface to display a risk of attrition and an intervention.

FIG. 18 illustrates a method to provide retention/attrition risk reduction recommendations. Data is extracted for caregiver C who worked N weeks in block 1805. Feature data is analyzed in block 1810. The attrition risk is predicted for caregiver C in the next M weeks in block 1815. A UI is generated representing a risk of attrition for caregiver C in block 1820. In block 1825, a display is generated of recommended retention/attrition risk reduction actions. The recommended actions may include making no changes in the treatment of caregiver C, such as if caregiver C has a low risk of attrition, is a low-rated employee (that the agency would be better off losing through attrition), or there are factors that suggest that an intervention would be ineffective. For example, if a caregiver is already at the maximum pay grade of the agency, a manager may not be permitted to make further pay increases to retain the caregiver. The recommended actions may be from a set of actions. Additionally, a recommend time for taking action may be provided. For example, an urgency factor may be generated indicating the time sensitivity for taking action (e.g., take recommended action within one hour, one day, or one week). For example, in the example of FIG. 17, a manager learning that he might be losing 20% of his staff may want to know what recommended actions to take with each caregiver and when to take them. For example, if 16 caregivers at high risk for attrition within 12 weeks, the manager may want to know which caregivers are most likely to have a reduction in their risk of attrition if he issues an immediate bonus check or pay raise to them, which caregivers are most likely to reduce their risk of attrition if he takes them to lunch the following week, and so.

In addition to action items to reduce the risk of attrition, another valuable form of business analytics for a manager or agency owner is information indicative of likelihood that available action items are unlikely to reduce the risk of attrition for one or more caregivers. Returning to the example of an agency in which there is high risk 16 caregivers will attrit in 12 weeks, suppose 4 of the caregivers are planning to return home to their country of origin for family reasons. There may be nothing the manager or agency owner can do that would significantly reduce the attrition risk of these caregivers. A bonus check, a pat on the back, or a pep talk may mean nothing to a caregiver whose elderly mother is a foreign country is sick. On the other hand, there may be 8 of the 16 caregivers at a high risk of attrition for which actions such as a small pay raise, more working hours, training, a pep talk, or other measures might dramatically reduce the risk of attrition.

Modifications and Variations to Use of Ensemble of Classifiers

Examples have been provided for using an ensemble of classifiers trained for different lengths of employment. It will be understood that further variations and refinements are theoretically possible, such as distinguishing between a length of time for full-time employment and part-time employment. Additionally, other attributes of a caregiver besides length of employment could be use to trigger a selection, from a set of differently trained classifiers.

Other Alternate Embodiments and Implementations

In the above description, for purposes of explanation, numerous specific details are set forth in order to provide a thorough understanding of the specification. It will be apparent, however, to one skilled in the art that the invention can be practiced without these specific details. In other instances, structures and devices are shown in block diagram form in order to avoid obscuring the description. For example, the present invention is described in one implementation below primarily with reference to user interfaces and particular hardware. However, the present invention applies to any type of computing system that can receive data and commands, and present information as part of a mobile device.

Reference in the specification to "one implementation" or "an implementation" means that a particular feature, structure, or characteristic described in connection with the implementation is included in at least one implementation of the description. The appearances of the phrase "in one implementation" in various places in the specification are not necessarily all referring to the same implementation.

Some portions of the detailed descriptions described above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present specification also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The specification can take the form of an entirely hardware implementation, an entirely software implementation or an implementation containing both hardware and software elements. In one implementation, the specification is implemented in software, which includes but is not limited to firmware, resident software, microcode, etc.

Furthermore, the description can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the specification is not described with reference to any particular programming language. It will be appreciated that a variety of programming languages may be used to implement the teachings of the specification as described herein.

The foregoing description of the implementations of the present invention has been presented for the purposes of illustration and description. It is not intended to be exhaustive or to limit the present implementation of invention to the precise form disclosed. Many modifications and variations are possible in light of the above teaching. It is intended that the scope of the present implementation of invention be limited not by this detailed description, but rather by the claims of this application. As will be understood by those familiar with the art, the present implementation of invention may be embodied in other specific forms without departing from the spirit or essential characteristics thereof. Likewise, the particular naming and division of the modules, routines, features, attributes, methodologies and other aspects are not mandatory or significant, and the mechanisms that implement the present implementation of invention or its features may have different names, divisions and/or formats. Furthermore, as will be apparent to one of ordinary skill in the relevant art, the modules, routines, features, attributes, methodologies and other aspects of the present implementation of invention can be implemented as software, hardware, firmware or any combination of the three. Also, wherever a component, an example of which is a module, of the present implementation of invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the present implementation of invention is in no way limited to implementation in any specific programming language, or for any specific operating system or environment. Accordingly, the specification of the present implementation of invention is intended to be illustrative, but not limiting, of the scope of the present implementation of invention, which is set forth in the following claims.

What is claimed is:

1. A method of generating retention information about caregivers responsible for in-home patient care, comprising:
    generating patient-caregiver interaction data by analyzing vocal communications occurring in interactions between patients and caregivers during in-home patient care monitored via a voice assistant disposed in a home of a patient having a home assistant configured for each caregiver to recognize speech patterns, participants in conversations, voice stress of each speaker, and words or phrases indicative of stress;
    generating caregiver satisfaction data including data associated with feedback caregivers enter from respective mobile devices of caregivers including at least one of caregiver surveys, hours worked, and clock-in/clock out data;
    predicting an attrition risk for each caregiver utilizing a machine learning system trained to determine an attrition risk probability for each caregiver based on features of the patient-caregiver interaction data and the caregiver satisfaction data, including features of the vocal communications between patients and caregivers during in-home patient care;
    generating, based on the attrition risk, a user interface having graphical elements representing a risk of attrition of individual caregivers providing in-home care of patients;
    wherein the machine learning system comprises an ensemble of classifiers to make predictions and the method includes making a population adaptive selection of a classifier, from an ensemble of classifiers, for each caregiver based at least in part on a length of time each caregiver has worked as a caregiver to account for a higher rate of attrition in an initial phase in employment of a caregiver;
    wherein each classifier in the ensemble of classifiers is trained to predict a risk of attrition for a different length of employment and the risk of attrition is determined for an individual caregiver by selecting a classifier, from the ensemble of classifiers, corresponding to the length of employment of the individual caregiver, and utilizing the selected classifier to predict the risk of attrition; and
    wherein the method comprises utilizing the ensemble of classifiers to predict a risk of attrition of an individual caregiver who has a current length of employment of N weeks will attrit within a next M weeks, where N and M are positive integers.

2. The method of claim 1, wherein caregiver satisfaction data comprises caregiver surveys, hours worked, and clock-in/clock out data.

3. A method of generating retention information about caregivers responsible for in-home patient care, comprising:
    generating patient-caregiver interaction data by analyzing vocal communications occurring in interactions between patients and caregivers during in-home patient care monitored via a voice assistant disposed in a home of a patient having a home assistant configured for each caregiver to recognize speech patterns, participants in conversations, voice stress of each speaker, and words or phrases indicative of stress;
    generating caregiver satisfaction data including data associated with feedback caregivers entered from respective mobile devices of caregivers;
        generating caregiver biometric data by analyzing data associated with at least one biometric sensor of a mobile device of caregivers indicative of stress of working with individual patients, wherein predicting an attrition risk for each caregiver comprises utilizing a machine learning system trained to determine an attrition risk probability for each caregiver based on features of the patient-caregiver data, the caregiver satisfaction data, and caregiver biometric data;
    predicting an attrition risk for each caregiver utilizing a machine learning system trained to determine an attrition risk probability for each caregiver based on features of the patient-caregiver interaction data and the caregiver satisfaction data, including features of the vocal communications between patients and caregivers during in-home patient care and the caregiver biometric data;
    generating, based on the attrition risk, a user interface having graphical elements representing a risk of attrition of individual caregivers providing in-home care of patients;
    wherein the machine learning system comprises an ensemble of classifiers to make predictions and the method includes making a population adaptive selection of a classifier, from an ensemble of classifiers, for each caregiver based at least in part on a length of time each caregiver has worked as a caregiver to account for a higher rate of attrition in an initial phase in employment of a caregiver;
    wherein each classifier in the ensemble of classifiers is trained to predict a risk of attrition for a different length of employment and the risk of attrition is determined for an individual caregiver by selecting a classifier, from the ensemble of classifiers, corresponding to the length of employment of the individual caregiver, and utilizing the selected classifier to predict the risk of attrition; and wherein the method comprises utilizing the ensemble of classifiers to predict a risk of attrition of an individual caregiver who has a current length of employment of N weeks will attrit within a next M weeks, where N and M are positive integers.

4. The method of claim 1, further comprising generating patient biometric data by analyzing biometric sensor readings of patients taken during in-home visits by caregivers, wherein predicting an attrition risk for each caregiver comprises utilizing a machine learning system trained to determine an attrition risk probability for each caregiver based on features of the patient-caregiver interaction data, the caregiver satisfaction data, and patient biometric data.

5. The method of claim 1, wherein the caregiver satisfaction data comprises data on whether or not caregivers feel appreciated.

6. The method of claim 1, wherein the user interface displays recommended action items for individual caregivers based on the attrition risk of each caregiver.

7. The method of claim 1, wherein the user interface displays information on caregiver having a high risk of attrition.

8. The method of claim 3, wherein the caregiver satisfaction data includes feedback caregivers enter from respective mobile devices of caregivers including caregiver surveys, hours worked, and clock-in/clock out data.

9. The method of claim 1, further comprising performing an intervention for a caregiver based on the attrition risk.

10. The method of claim 9, wherein the intervention comprises at least one member from the group consisting of praise and a pay raise.

11. The method of claim 3, wherein the caregiver satisfaction data includes feedback caregivers entered from respective mobile devices of caregivers including at least one of caregiver surveys, hours worked, and clock-in/clock out data.

12. A method of generating retention information about caregivers responsible for in-home patient care, comprising:

generating patient-caregiver interaction data by analyzing vocal communications occurring in interactions between patients and caregivers during in-home patient care monitored via audio or audiovisual sensors disposed in a home of a patient;

generating caregiver satisfaction data by analyzing data associated with feedback caregivers entered from respective mobile devices of the caregivers including caregiver surveys, hours worked, and log-in, log-out data;

generating patient satisfaction data by analyzing data associated with patient feedback on individual caregivers;

predicting an attrition risk for each caregiver utilizing a machine learning system trained to determine an attrition risk probability for each caregiver based on features of the patient-caregiver interaction data, the caregiver satisfaction data; and the patient satisfaction data;

generating, based on the attrition risk, a user interface having graphical elements representing a risk of attrition of individual caregivers providing in-home care of patients;

displaying, on the user interface, factors contributing to a risk of attrition of individual caregivers;

displaying recommended action items for individual caregivers based on the attrition risk of each caregiver;

wherein the machine learning system comprises an ensemble of classifiers to make predictions and the method includes making a population adaptive selection of a classifier, from an ensemble of classifiers, for each caregiver based at least in part on a length of time each caregiver has worked as a caregiver to account for a higher rate of attrition in an initial phase in employment of a caregiver;

wherein each classifier in the ensemble of classifiers is trained to predict a risk of attrition for a different length of employment and the risk of attrition is determined for an individual caregiver by selecting a classifier, from the ensemble of classifiers, corresponding to the length of employment of the individual caregiver, and utilizing the selected classifier to predict the risk of attrition; and wherein the method comprises utilizing the ensemble of classifiers to predict a risk of attrition of an individual caregiver who has a current length of employment of N weeks will attrit within a next M weeks, where N and M are positive integers.

13. The method of claim 12, further comprising caregiver biometric data by analyzing data associated with at least one biometric sensor of a mobile device of caregivers indicative of stress of working with individual patients, wherein predicting an attrition risk for each caregiver comprises utilizing a machine learning system trained to determine an attrition risk probability for each caregiver based on features of the patient-caregiver interaction data, the caregiver satisfaction data, and caregiver biometric data.

14. The method of claim 12, further comprising generating patient biometric data by analyzing biometric sensor readings of patients taken during in-home visits by caregivers, wherein predicting an attrition risk for each caregiver comprises utilizing a machine learning system trained to determine an attrition risk probability for each caregiver based on features of the patient-caregiver interaction data, the caregiver satisfaction data, and patient biometric data.

15. The method of claim 12, wherein the caregiver satisfaction data comprises data on whether or not caregivers feel appreciated.

16. The method of claim 12, wherein the user interface displays information on a caregiver having a high risk of attrition.

17. The method of claim 12, further comprising performing an intervention for a caregiver based on the attrition risk.

18. The method of claim 17, wherein the intervention comprises at least one member from the group consisting of praise and a pay raise.

19. The method of claim 1, wherein predicting the attrition risk further comprises analyzing features of feedback from caregivers, people being cared for, families of people being cared for, and managers or schedulers of caregivers; caregiver employment data, caregiver work performance, and caregiver work satisfaction.

* * * * *